(12) United States Patent
Kam et al.

(10) Patent No.: US 10,301,590 B2
(45) Date of Patent: May 28, 2019

(54) METHODS, COMPOSITIONS, AND SYSTEMS FOR ACTIVATION AND EXPANSION OF CELLS

(71) Applicant: The Trustees of Columbia University in the City of New York, New York, NY (US)

(72) Inventors: Lance C. Kam, New York, NY (US); Helen H. Lu, New York, NY (US); Sarah E. De Leo, Baton Rouge, LA (US); Keenan T. Bashour, Hillsborough, CA (US); Danielle Bogdanowicz, Cortlandt Manor, NY (US); Philip Chuang, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 102 days.

(21) Appl. No.: 15/302,475

(22) PCT Filed: Apr. 10, 2015

(86) PCT No.: PCT/US2015/025355
§ 371 (c)(1),
(2) Date: Oct. 6, 2016

(87) PCT Pub. No.: WO2015/157664
PCT Pub. Date: Oct. 15, 2015

(65) Prior Publication Data
US 2017/0029767 A1    Feb. 2, 2017

Related U.S. Application Data

(60) Provisional application No. 61/977,913, filed on Apr. 10, 2014, provisional application No. 62/066,483, filed on Oct. 21, 2014, provisional application No. 62/111,184, filed on Feb. 3, 2015.

(51) Int. Cl.
| | |
|---|---|
| C12N 5/00 | (2006.01) |
| A61K 35/17 | (2015.01) |
| D04B 21/12 | (2006.01) |
| D06M 15/15 | (2006.01) |
| C12N 5/0775 | (2010.01) |
| C12N 5/0783 | (2010.01) |
| D06M 101/30 | (2006.01) |
| D06M 101/32 | (2006.01) |

(52) U.S. Cl.
CPC ............ *C12N 5/0075* (2013.01); *A61K 35/17* (2013.01); *C12N 5/0068* (2013.01); *C12N 5/0636* (2013.01); *C12N 5/0662* (2013.01); *D04B 21/12* (2013.01); *D06M 15/15* (2013.01); *C12N 2531/00* (2013.01); *C12N 2533/30* (2013.01); *C12N 2533/40* (2013.01); *C12N 2533/50* (2013.01); *D06M 2101/30* (2013.01); *D06M 2101/32* (2013.01)

(58) Field of Classification Search
CPC .............. C12N 5/0075; C12N 2531/00; C12N 2533/30; C12N 2533/40; D04B 21/12
See application file for complete search history.

(56) References Cited

U.S. PATENT DOCUMENTS

| | | | |
|---|---|---|---|
| 4,911,718 A | 3/1990 | Lee et al. | |
| 6,887,974 B2* | 5/2005 | Pathak | ................. A61K 9/0014 525/54.1 |
| 7,998,736 B2 | 8/2011 | Morgan et al. | |
| 2003/0194395 A1 | 10/2003 | Gruenberg et al. | |
| 2004/0115216 A1 | 6/2004 | Schneck et al. | |
| 2005/0118599 A1 | 6/2005 | Pawliszyn | |
| 2005/0276727 A1 | 12/2005 | Pawliszyn et al. | |
| 2010/0068193 A1 | 3/2010 | Brunsvig et al. | |
| 2010/0129392 A1 | 5/2010 | Shi et al. | |
| 2011/0097339 A1 | 4/2011 | Holmes et al. | |
| 2011/0196328 A1 | 8/2011 | Bellini et al. | |
| 2013/0214457 A1 | 8/2013 | David et al. | |
| 2014/0322512 A1* | 10/2014 | Pham | ....................... D01F 8/16 428/220 |

FOREIGN PATENT DOCUMENTS

| | | |
|---|---|---|
| EP | 1827604 A1 | 9/2007 |
| GB | 2504996 A | 2/2014 |
| WO | 2013036585 A1 | 3/2013 |
| WO | 2014145745 A2 | 9/2014 |

OTHER PUBLICATIONS

Norman et al., Annals of Biomedical Engineering, 2006, vol. 34, No. 1, p. 89-101.*
Norman et al., Tissue Engineering, 2005, vol. 11, No. 3/4, p. 378-386.*
Shin et al., Biomaterials, 2004, vol. 25, p. 3717-3723.*
Part et al., Journal of Nanonnaterials, 2011, vol. 2011, Article ID 201969, 9 pages.*
Bhuvania, "Substrate Stiffness Adjustable PDMS Device/Array for Understanding its Effect on Cell Growth, Differentiation and Migration", Presented to the Faculty of the Graduate School of The University of Texas at Arlington in Partial Fulfillment of the Requirements for the Degree of Master of Science in Biomedical Engineering the University of Texas At Arlington, Aug. 1, 2011, 72 pages.

(Continued)

*Primary Examiner* — Kade Ariani
(74) *Attorney, Agent, or Firm* — Potomac Law Group, PLLC; Mark Catan

(57) ABSTRACT

The disclosure provides for compositions, systems, and methods of cell expansion, stimulation and/or differentiation. The disclosure further provides for a mesh substrate and associated methods capable of stimulating cell expansion, for example, T cell or stem cell expansion. In another aspect, the disclosure provides for an electrospun mesh substrate and methods of using thereof comprising a silicone rubber composition, for example, polydimethylsiloxane, PLC, or combinations thereof.

26 Claims, 33 Drawing Sheets

(56) References Cited

OTHER PUBLICATIONS

Communication pursuant to Article 94(3) EPC for European Patent Application No. 15776853.2 dated Oct. 25, 2017.
International Preliminary Report on Patentability for International Application No. PCT/US2015/025355 dated Oct. 12, 2016.
Bogdanowicz et al.; "Poly(dimethyl siloxane)—Containing Nanofiber Meshes as a Platform for Studying Stem Cell Behavior," Jan. 1, 2015, retrieved from the Internet: http://2015.biomaterials.org/sites/default/files/abstracts/136.pdf.
Rao et al, "Mimicking white matter tract topography using core-shell electrospun nanofibers to examine migration of malignant brain tumors", Biomaterials, Apr. 16, 2013, vol. 34(21), pp. 5181-5190.
Written Opinion of the International Searching Authority of PCT/US2015/025355 dated Oct. 12, 2016.
Berger et al., "CD28 costimulation and immunoaffinity-based selection efficiently generate primary gene-modified T cells for adoptive immunotherapy," Blood, vol. 101, Issue 2, pp. 476-484, Jan. 2003.
Doshi et al., "Electrospinning process and applications of electrospun fibers," J. Electrostatics, vol. 35, Issues 2-3, pp. 151-160, Aug. 1995.
Gattinoni et al., "Adoptive immunotherapy for cancer: building on success," Nat. Rev. Immunol., vol. 6, Issue 5, pp. 383-393, May 2006.
June, "Principles of adoptive T cell cancer therapy," The Journal of Clinical Investigation, vol. 117, No. 5, pp. 1204-1212, May 2007.

\* cited by examiner

A.

| PDMS: Curing agent | PDMS: PCL | Fiber Diameter (nm) | Pore Size (μm) | UTS (MPa) | Elastic Modulus (MPa) |
|---|---|---|---|---|---|
| N/A | 0:4 | 559.50 ± 257.86 * | 2.75 ± 0.45 | 4.31± 0.61 | 20.02 ± 2.44 * |
| 10:1 | 1:1 | 383.38 ± 163.30 # | 1.9 ± 0.46 | 4.55 ± 0.14 | 4.67 ± 0.80 |
| 10:1 | 4:1 | 293 ± 104 | 1.48 ± 0.79 | | |
| 50:1 | 1:1 | 264.58 ± 94.09 | 2.21 ± 0.38 | 3.52 ± 0.31 | 3.85 ± 0.45 |
| 50:1 | 4:1 | 248.52 ± 131.06 | 2.48 ± 0.52 | 4.98 ± 1.22 | 5.56 ± 0.86 |

| Day 3 | % Cell Divided | Prolif. Index |
|---|---|---|
| 1:50 PDMS 4:1 PCL | 25.4 | 1.85 |
| 1:10 PDMS 4:1 PCL | 38.4 | 1.71 |
| 1:50 PDMS 1:1 PCL | 30.8 | 1.76 |
| 1:10 PDMS 1:1 PCL | 23.5 | 1.88 |
| Positive Control Dynabeads | 47.3 | 1.44 |
| Negative Control | 0 | 0 |

| | Sample | Percent Divided | Proliferation Index |
|---|---|---|---|
| A | D – 50:1 1:1 nano unaligned | 67.6 | 2.97 |
| B | V – 50:1 1:1 micro unaligned | 57.5 | 2.87 |
| C | W – 50:1 1:1 micro aligned | 65.1 | 3.11 |
| D | L – 50:1 4:1 nano aligned | 68.5 | 3.06 |
| E | E1 – 50:1 1:1 nano unaligned | 67.3 | 2.69 |
| F | T – PCL unaligned | 59.5 | 2.78 |
| G | U – PCL aligned | 67.4 | 3.22 |
| H | (+) Dynabeads® (3:1) | 76.6 | 2.60 |
| I | (–) No stimulation | 0.0 | 1.00 |

| Mesh Type | PDMS : PCL (w/w) Target diameter | Alignment | Fiber Diameter (μm) | Pore Radius (μm) |
|---|---|---|---|---|
| 1 – Low Micro UA | 1:1 Micro | Unaligned | 2.12 ± 0.64 | 9.88 ± 1.97 |
| 2 – Low Micro A | 1:1 Micro | Aligned | 2.28 ± 0.39 | 11.71 ± 2.12 |
| 3 – High Micro UA | 2.5:1 Micro | Unaligned | 2.14 ± 0.50 | 12.21 ± 3.37 |
| 4 – High Micro A | 2.5:1 Micro | Aligned | 1.02 ± 0.30 | 10.04 ± 4.34 |
| 5 – High Nano UA | 3:1 Nano | Unaligned | 0.74 ± 0.27 | 3.07 ± 0.73 |
| 6 – High Nano A | 3:1 Nano | Aligned | 0.68 ± 0.29 | 2.51 ± 0.80 |
| 7 – PCL Micro UA | Pure PCL Micro | Unaligned | 1.05 ± 0.22 | 8.19 ± 1.77 |
| 8 – Dynabeads® | | | 4.5 | |
| 9 – Primary Stim | | not previously expanded | | |

METHODS, COMPOSITIONS, AND SYSTEMS FOR ACTIVATION AND EXPANSION OF CELLS

CROSS-REFERENCE TO RELATED APPLICATIONS

This application is a U.S. national stage filing under 35 U.S.C. § 371 of International Application No. PCT/US2015/25355, filed Apr. 10, 2015, the content of which is hereby incorporated by reference in its entirety, which claims priority to U.S. Provisional Application No. 61/977,913, filed Apr. 10, 2014, U.S. Provisional Application No. 62/066,483, filed Oct. 21, 2014, and U.S. Provisional Application No. 62/111,184, filed Feb. 3, 2015, the contents of which are hereby incorporated herein by reference in their entireties.

STATEMENT REGARDING FEDERALLY-SPONSORED RESEARCH

This invention was made with government support under grants EY016586 and AI110593 awarded by the National Institutes of Health, and grant 1144155 awarded by the National Science Foundation. The Government has certain rights in the invention.

FIELD

The disclosure provides for compositions, systems, and methods of cell expansion, stimulation and/or differentiation. The disclosure further provides for a mesh substrate and associated methods capable of stimulating cell expansion, for example, T cell and/or stem cell expansion. In another aspect, the disclosure provides for electrospun mesh substrates comprising a silicone rubber composition, for example, polydimethylsiloxane, polycaprolactone, or combinations thereof and associated methods of proliferating cell expansion using electrospun mesh substrates described herein.

BACKGROUND

Adoptive immunotherapy holds great potential as a therapeutic modality for the treatment of a variety of diseases including cancer and chronic viral infections. Central to these therapeutic approaches are controllable platforms for ex vivo activation of T cells. Several cell-based and artificial substrate systems have been described (June, 2007, J Clin Invest. 117(5): 1204-12).

Agonist antibodies to CD3 and CD28 immobilized on rigid materials, for example, polystyrene plastic and glass, have been utilized for the activation and expansion of T cells. However, T cells are unlikely to encounter a stimulatory surface with the stiffness of plastic in vivo, and the stiffness of the solid supports used for ex vivo culture of T cells may have important influences on their activation, proliferation, and differentiation that could impact their use in adoptive immunotherapy.

Current immunotherapy technologies reprogram T cells ex vivo to target leukemia. During this process, cells are transfected and expanded. One such method for facilitating T cell expansion involves Dynabeads™, for example, 4.5-um diameter polystyrene beads mixed with cells for high surface area-to-volume ratio. T cell signaling, proliferation, and expansion has been linked to the rigidity of the surface on which they are cultured—finding optimal expansion on "softer" surfaces (Young's Modulus or elastic modulus, "E," of bulk materials less than 100 kPa as compared to a Young's Modulus, E, of greater than 2 MPa).

However, there is a need to develop further expansion platforms that allow for the fine-tuning of surface and/or matrix rigidity while maintaining a high area-to-volume ratio, which can be important to cell culture and practicality of clinical use. To this end, the electrospun mesh described herein offers an improved area-to-volume ratio and has many parameters that can be altered to tune rigidity and additional properties of interest, for example, polymer composition, fiber diameter, and mesh porosity.

SUMMARY

In an aspect, the disclosure provides for a method of improving cell expansion comprising culturing cells on a mesh substrate described herein. In another aspect, the cells are T cells and/or stem cells.

In an aspect, the mesh substrate comprises and/or is spun from one or more of a synthetic polymer or copolymer prepared from at least one of the group of monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, .e-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-aminostyrene, p-amino-benzyl-styrene, sodium styrene sulfonate, sodium 2-sulfoxyethyl methacrylate, vinyl pyridine, aminoethyl methacrylates, 2-methacryloyloxytrimethylammonium chloride, N,N'-methylenebisacrylamide-, ethylene glycol dimethacrylates, 2,2'-(p-phenylenedioxy)-diethyl dimethacrylate, divinylbenzene, triallylamine, and methylenebis-(4-phenyl-isocyanate).

In another aspect, the disclosure provides for a mesh substrate comprising and/or spun from polydimethylsiloxane and polycaprolactone.

The disclosure also provides for a mesh substrate including fibers with a diameter of about 10 nm to about 1000 nm and a pore size of about 0.5 μm to about 100 μm. In another aspect, the disclosure provides for a mesh substrate including fibers with a diameter of about 10 nm to about 2000 nm or a diameter of about 10 nm to about 5000 nm. The disclosure further provides for a mesh substrate including fibers with a diameter of up to about 1000 nm, about 2000 nm, about 3000 nm, or about 5000 nm.

Further, the disclosure also provides for a mesh substrate including fibers with a diameter selected from the group consisting of about 25 nm to about 1000 nm, about 50 nm to about 750 nm, about 100 nm to about 500 nm, about 500 to about 800 nm, about 250 to about 1000 nm, about 1000 to about 2500 nm, about 200 nm to about 5000 nm, 100 nm to 20 μm, 300 nm to about 10 μm.

In another aspect, the disclosure provides for a mesh substrate comprising fibers with a pore size selected from the group consisting of about 1 μm to about 100 μm, about 1 μm to about 50 μm, about 1 μm to about 10 μm, and about 1 μm to about 5 μm.

The disclosure also provides for a substrate comprising polydimethylsiloxane and polycaprolactone in a ratio (w/w) selected from the group consisting of about 5:1, about 3:1, about 2.5:1, about 2:1, about 1:1, about 1:2, about 1:2.5, and about 1:5. In another aspect, the ratio of components can be modified in order to modify rigidity.

In an aspect, the cell expansion, for example stem cell or T-cell expansion, on a mesh substrate comprising polydimethylsiloxane and polycaprolactone is improved relative to polycaprolactone alone. In another aspect, cell expansion on a mesh substrate comprising polydimethylsiloxane and polycaprolactone is improved relative to polycaprolactone alone by at least about 10%, 20%, 30%, 40%, 50%, 60%, and 75%.

BRIEF DESCRIPTION OF THE FIGURES

FIG. 6 provides for the percentage of cells divided and proliferation index for mesh spun from PDMS-A and PCL for a variety of ratios.

FIG. 16 provides for a table of cell proliferation index under various conditions for SYLGARD 184 fiber mesh substrate.

FIG. 26 provides for an mesh according to the description to Dynabeads™ comparison under various conditions with a cell source of Primary human CD4/CD8 T cells from leukopacks. "UA" refers to unaligned and "A" refers to aligned. The diameter of the fibers specified as "nano" refers to fibers in the sub-micrometer range, for example 600-700 nm for the data presented, and "micro" are in the single micrometer diameter range, for example, 1-2 μm for the data presented. "Low micro" refers to about a 1:1 PDMS:PCL ratio while "high micro" refers to about a 3:1 or about a 2.5:1 ratio of PDMS:PCL.

DETAILED DESCRIPTION

Compositions, Systems, and Methods

Figure 1:
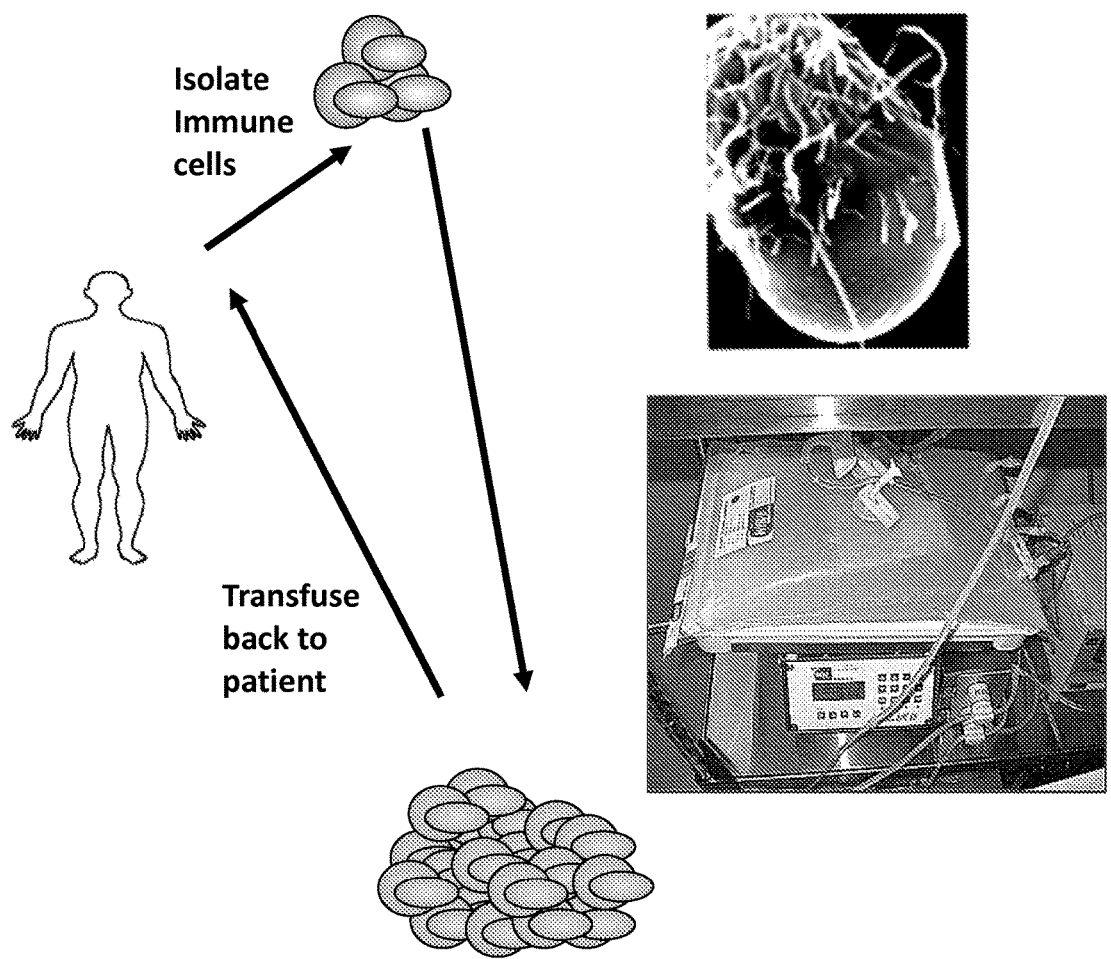
FIG. 1 provides for an example cell expansion methodology whereby immune cells are isolated from an individual, the cells are expanded in vitro by a method described herein, and the cells are transfused back to an individual in need thereof.
Figure 2:
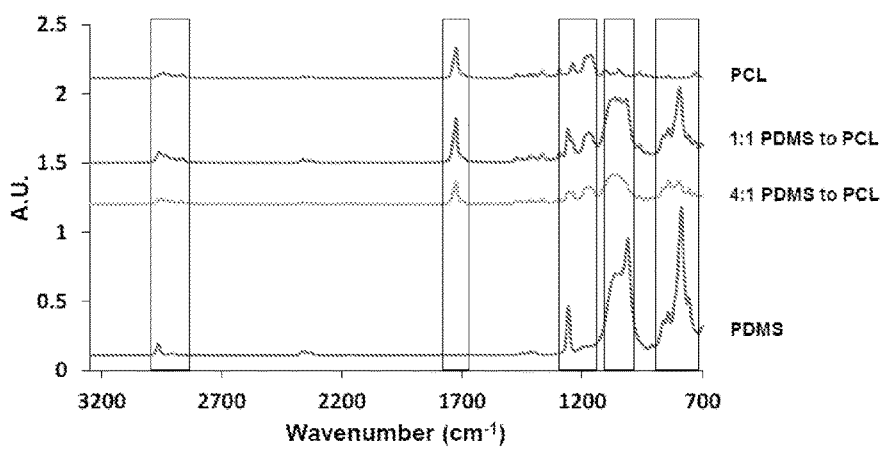
FIG. 2 provides for (A) a graphical representation of polycaprolactone ("PCL"), a 1:1 ratio of polydimethylsiloxane ("PDMS-A") and PCL, a 4:1 ratio of PDMS and PCL, and PDMS and (B) fiber diameter, pore size, UTS (MPa), and elastic modulus (MPa) for various PDMS curing agent ratios together with various PDMS to PCL ratios.

In an aspect, the disclosure provides for compositions, systems, and methods of cell expansion, stimulation and/or differentiation. The disclosure further provides for a substrate, for example a mesh substrate, and associated methods capable of stimulating cell expansion, for example, T cell expansion. In another aspect, the disclosure provides for an electrospun mesh substrate comprising a silicone rubber composition, for example, polydimethylsiloxane ("PDMS"). In yet another aspect, the disclosure provides for an electrospun mesh substrate comprising PDMS, PLC, or combinations thereof. In a further aspect, the disclosure provides for an electrospun mesh substrate comprising, consisting of, or consisting essentially of PDMS and PLC. In an aspect, the disclosure provides for improved cell proliferation with a PDMS:PCL mesh as compared to a mesh with PCL alone. In another example, the disclosure provides for a fibrous mesh substrate preserves the high surface area to volume ratio associated with beads while greatly reducing the risks associated with bead-cell separation.

In an aspect, optimization of this methodology described herein is performed by exposing cells, for example T cells and/or stem cells, to meshes of varying rigidities, fiber diameters, and mesh densities over periods ranging from 3 to 17 days or 5 to 25 days.

In one embodiment, the substrate described herein exhibits an elastic modulus ranging from about 25 kPa to about 10 MPa. In another embodiment, the substrate described herein exhibits an elastic modulus ranging from about 1 MPa to about 5 MPa, about 2 MPa to about 8 MPa, about 2 MPa to about 10 MPa, about 1 MPa to about 30 MPa, about 2 MPa to about 25 MPa, about 5 MPa to about 25 MPa, about 5 MPa to about 10 MPa.

In yet another embodiment, the substrate described herein exhibits a fiber diameter of about 10 nm to about 20 µm, about 100 nm to about 10 µm, about 25 nm to about 1000 nm, about 50 nm to about 750 nm, about 100 nm to about 500 nm, or about 200 nm to about 500 nm. In another embodiment, the substrate described herein exhibits a pore size of about 1 µm to about 100 µm, about 1 µm to about 50 µm, about 1 µm to about 10 µm, about 1 µm to about 5 µm, about 0.5 µm to about 5 µm, about 0.5 µm to about 4 µm, about 1 µm to about 4 µm, about 1 µm to about 3 µm, about 1 µm to about 2.5 µm, about 1.5 µm to about 2.5 µm. In an aspect, stem cell proliferation is not fiber diameter dependent and the diameter can be below 10 nm and above 10 µm.

In an aspect, a mesh substrate described herein is spun in PDMS and PCL ratios described in Tables 1-3 and FIGS. 2, 6, 12, 13, 15, 16, 19, 20, and 26. In another aspect, a mesh substrate described herein is spun in PDMS and PCL in ratios described in Tables 1-3 and FIGS. 2 and 6 and exhibits an elastic modulus, fiber diameter, and/or pore size described herein.

In yet another aspect, mesh spun from 1:10 PDMS in a 1:1 and 4:1 ratio with PCL and exhibits nano-scale fiber diameters, with micro-scale pores. In an aspect, the disclosure provides for a ratio of PDMS:PCL (w/w) from about 5:1, 3:1, 2.5:1, 2:1, 1:1, 1:2, 1:3, 1:4, and 1:5. In another aspect, the ratio is selected based on target fiber.

Figure 27:
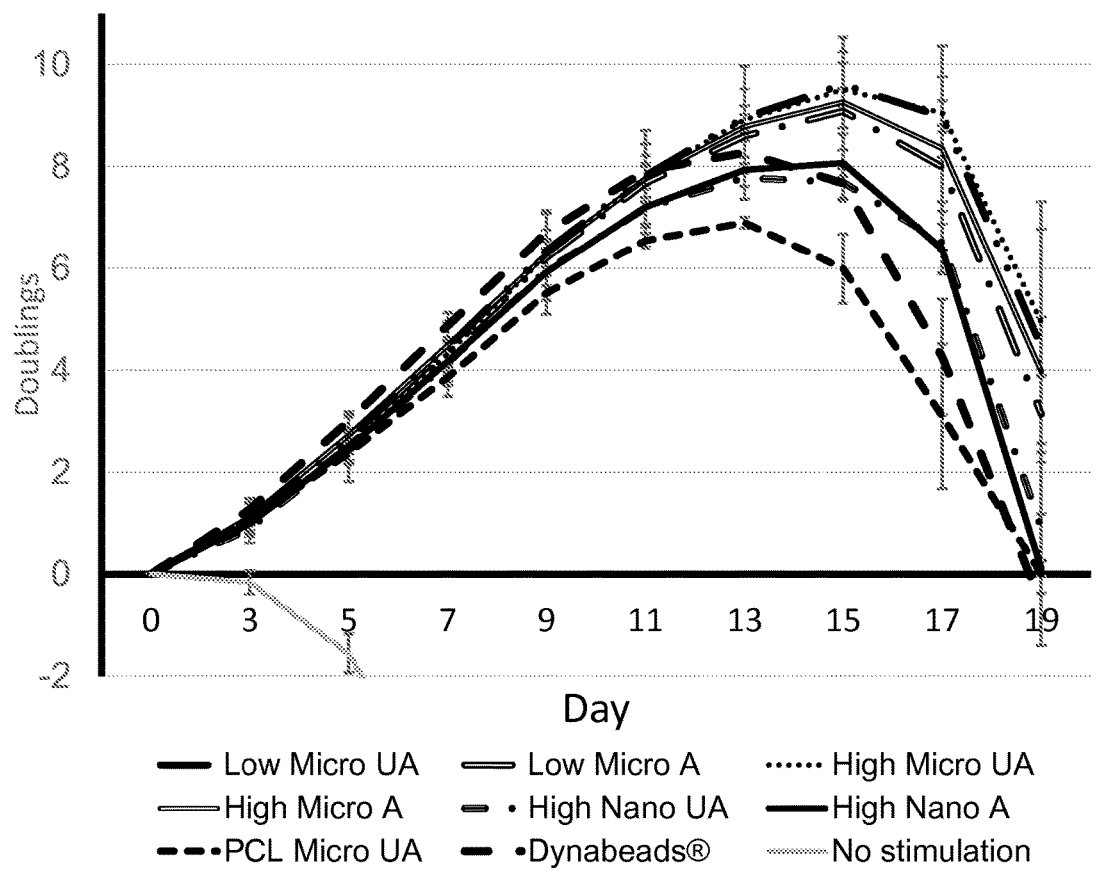
FIG. 27 provides for a graph of cell proliferation, indicating improved cell expansion on mesh according to the description under various conditions. "UA" refers to unaligned and "A" refers to aligned. When indicated, data are mean±s.d. (n=3). "Low micro" refers to about a 1:1 PDMS:PCL ratio while "high micro" refers to about a 3:1 or about a 2.5:1 ratio of PDMS:PCL. The diameter of the fibers specified as "nano" refers to fibers in the sub-micrometer range, for example 600-700 nm for the data presented, and "micro" are in the single micrometer diameter range, for example, 1-2 µm for the data presented.
Figure 28:
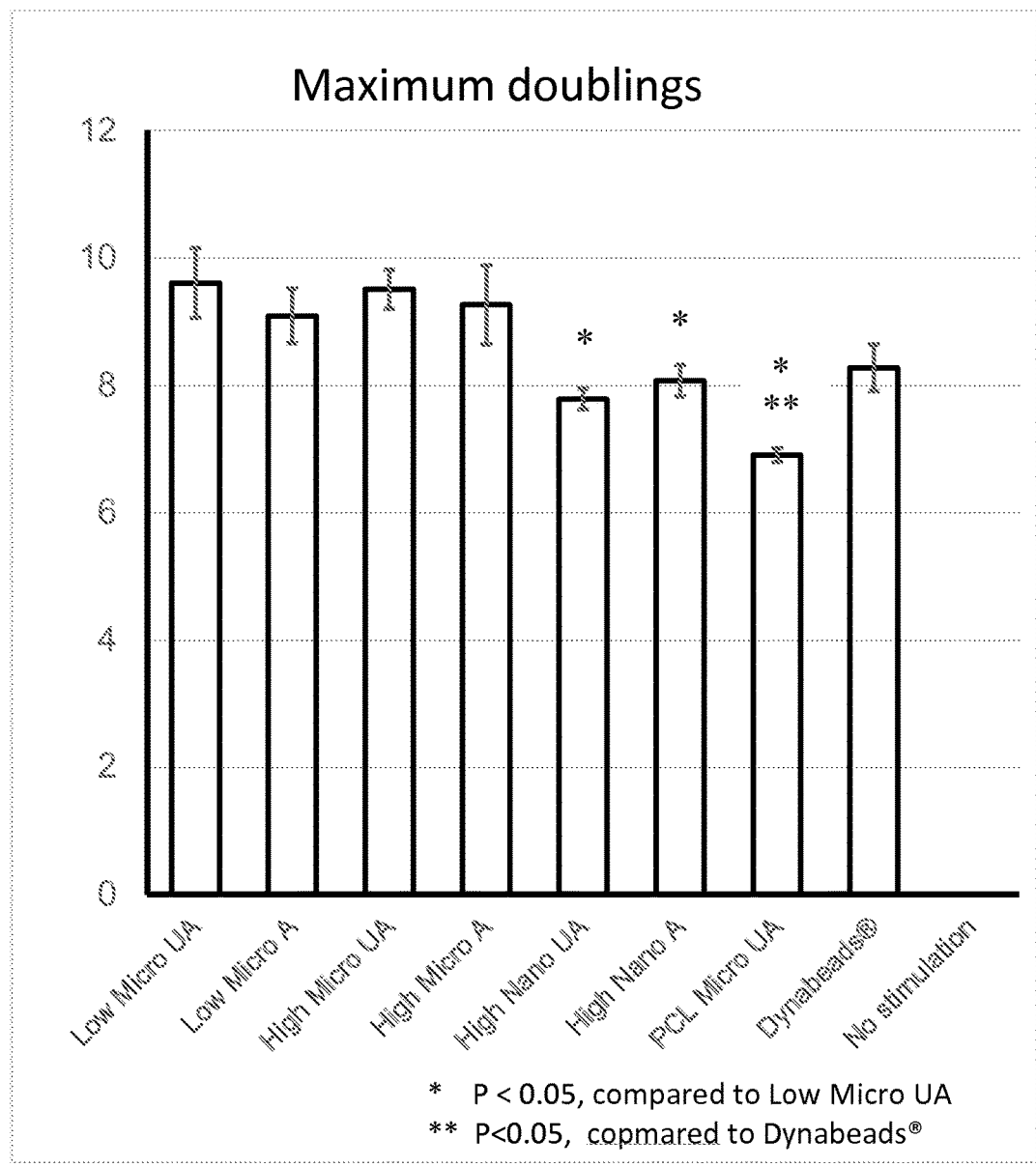
FIG. 28 indicates improved cell expansion on mesh according to the description under various conditions. "UA" refers to unaligned and "A" refers to aligned. When indicated, data are mean±s.d. (n=3). "Low micro" refers to about a 1:1 PDMS:PCL ratio while "high micro" refers to about a 3:1 or about a 2.5:1 ratio of PDMS:PCL. The diameter of the fibers specified as "nano" refers to fibers in the sub-micrometer range, for example 600-700 nm for the data presented, and "micro" are in the single micrometer diameter range, for example, 1-2 µm for the data presented.
Figure 29:
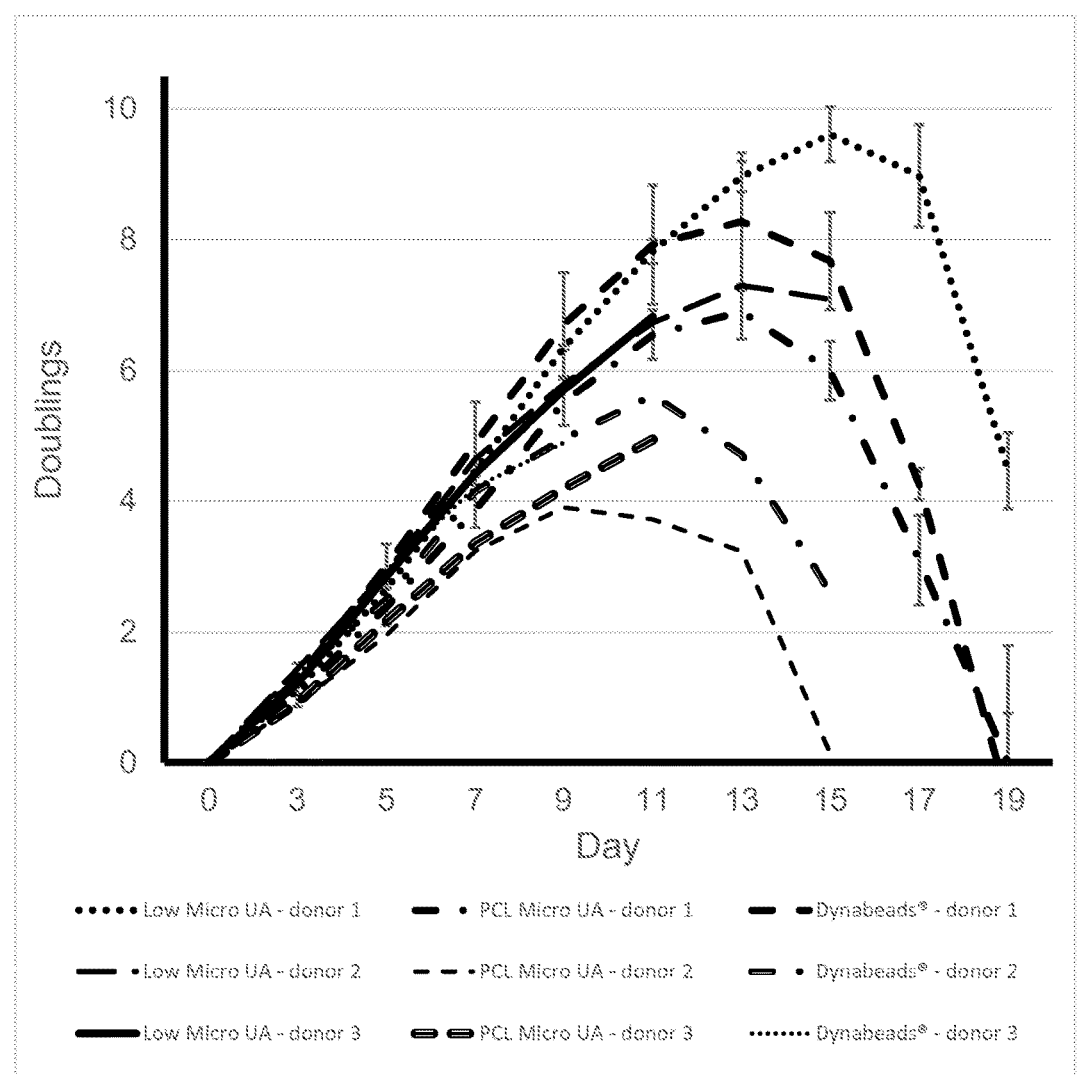
FIG. 29 provides for a graph of cell proliferation under various conditions. "UA" refers to unaligned and "A" refers to aligned. When indicated, data are mean±s.d. (n=3). "Low micro" refers to about a 1:1 PDMS:PCL ratio while "high micro" refers to about a 3:1 or about a 2.5:1 ratio of PDMS:PCL. The diameter of the fibers specified as "nano" refers to fibers in the sub-micrometer range, for example 600-700 nm for the data presented, and "micro" are in the single micrometer diameter range, for example, 1-2 µm for the data presented.
Figure 30:
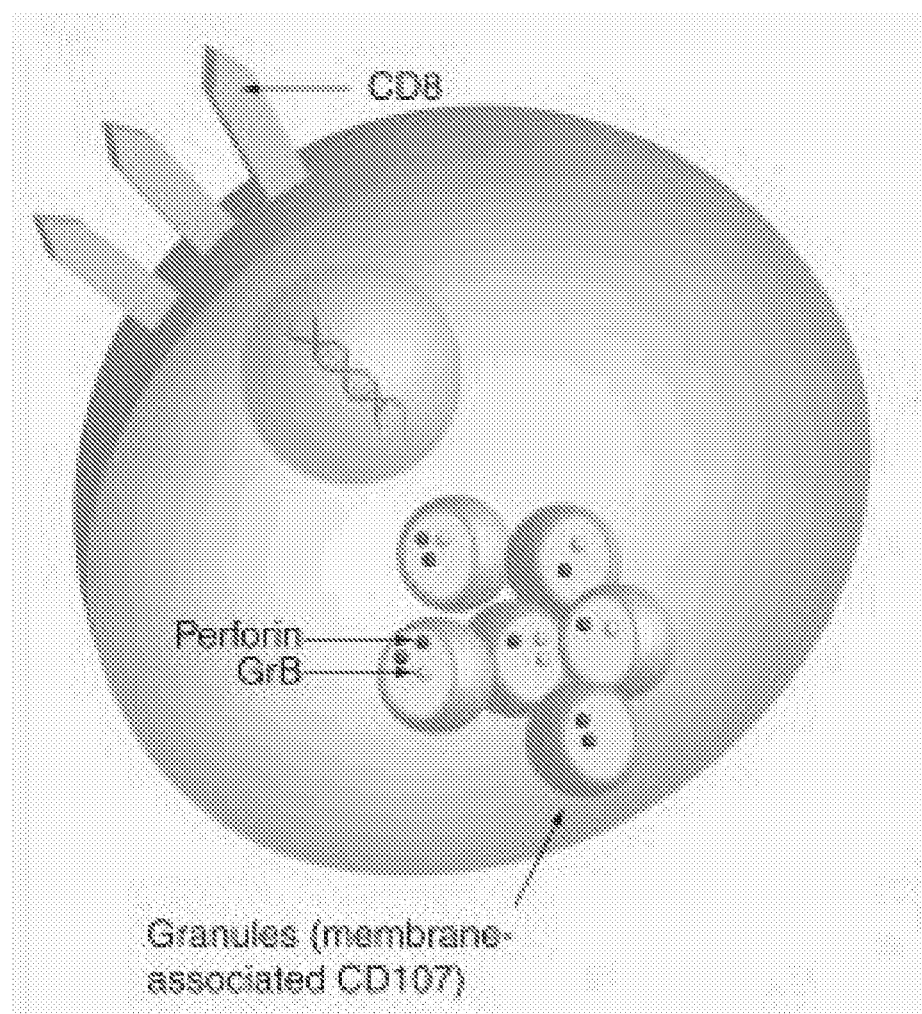
FIG. 30 provides for a representative schematic of Lysosome-associated membrane glycoprotein 2 (LAMP2) mobilization.
Figure 31:
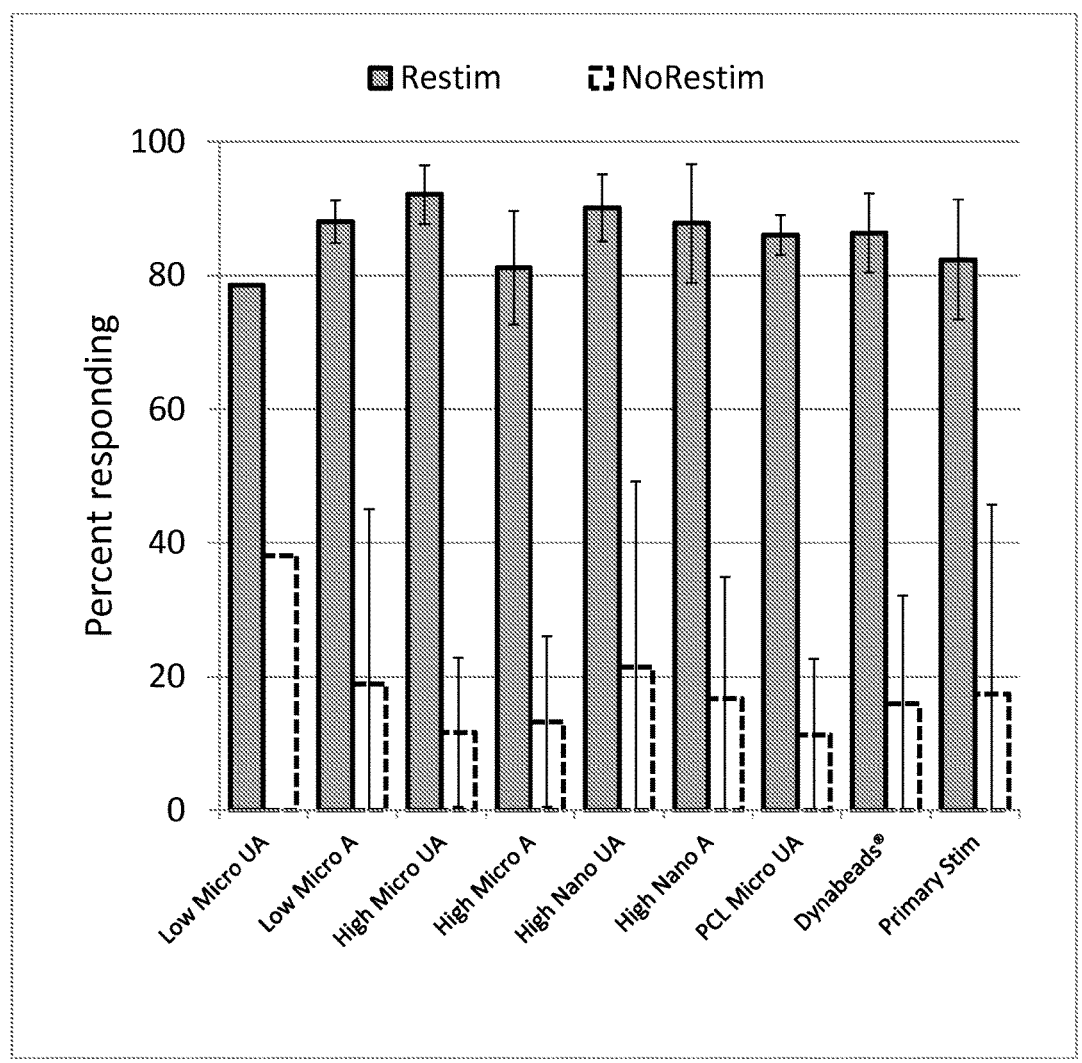
FIG. 31 indicates the number of cells responding with and without restimulation under various conditions Restimulation refers to activation of T cells after expansion. This figure further confirms the functionality of cells expanded on mesh according to the description. "UA" refers to unaligned and "A" refers to aligned. "Low micro" refers to about a 1:1 PDMS:PCL ratio while "high micro" refers to about a 3:1 or about a 2.5:1 ratio of PDMS:PCL. The diameter of the fibers specified as "nano" refers to fibers in the sub-micrometer range, for example 600-700 nm for the data presented, and "micro" are in the single micrometer diameter range, for example, 1-2 µm for the data presented.
Figure 32:
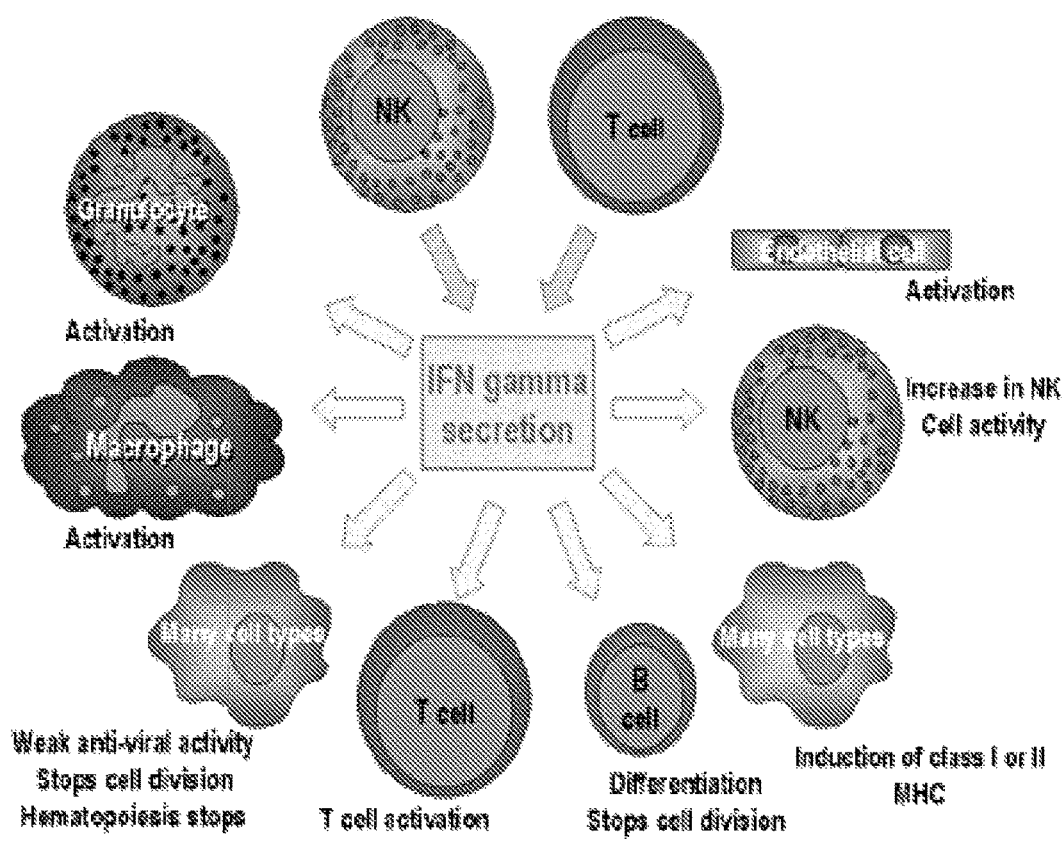
FIG. 32 provides for a schematic of Interferon gamma (IFNγ) secretion.
Figure 33:
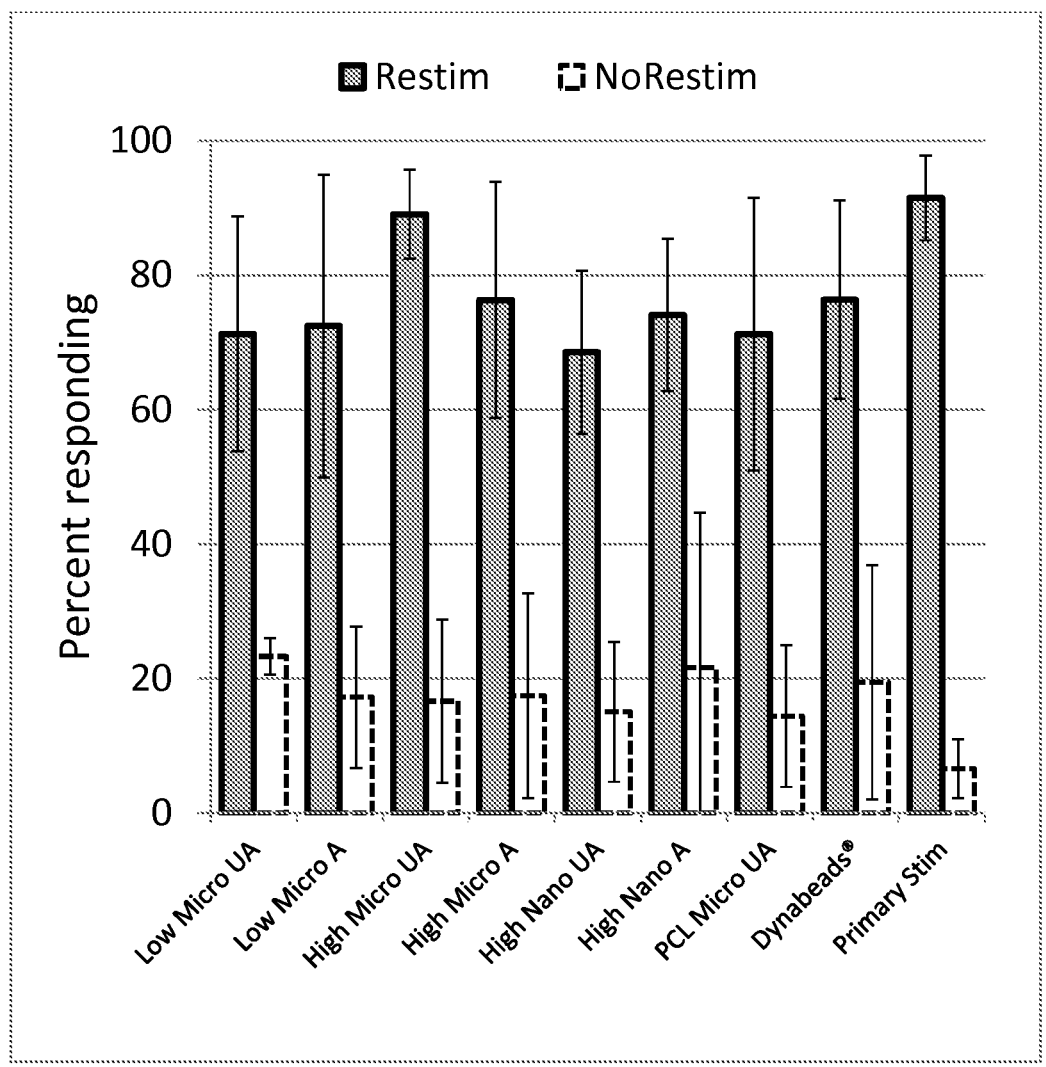
FIG. 33 indicates the percentage of cells responding with and without restimulation under various conditions. This figure further confirms the functionality of cells expanded on mesh according to the description. "Low micro" refers to about a 1:1 PDMS:PCL ratio while "high micro" refers to about a 3:1 or about a 2.5:1 ratio of PDMS:PCL. The diameter of the fibers specified as "nano" refers to fibers in the sub-micrometer range, for example 600-700 nm for the data presented, and "micro" are in the single micrometer diameter range, for example, 1-2 µm for the data presented.

In an aspect, microscale fiber meshes, such as those in FIGS. 27-29, exhibited improved cell expansion relative to nanoscale meshes. In another aspect, unaligned fibers exhibit increased cell expansion over aligned mesh according to the description.

In an aspect, cell expansion, for example T-cell or Stem cell on a mesh substrate comprising polydimethylsiloxane and polycaprolactone is improved by about 10%, about 20%, about 30%, about 40%, about 50%, about 60%, or about 75% relative to polycaprolactone alone. In another aspect, cell expansion, for example T-cell or Stem cell on a mesh substrate comprising polydimethylsiloxane and polycaprolactone is improved by at least about 10%, at least about 20%, at least about 30%, at least about 40%, at least about 50%, at least about 60%, or at least about 75% relative to polycaprolactone alone. In another aspect, cell expansion, for example T-cell or Stem cell on a mesh substrate comprising polydimethylsiloxane and polycaprolactone is improved by about 10% to about 75%, about 10% to about 30%, about 20% to about 50%, about 30% to about 50% relative to polycaprolactone alone.

In an aspect, cell expansion using a silicone rubber meshes described herein is enhanced relative to cell expansion utilizing beads, for example Dynabeads™ (Dynal AS). In another aspect, cell expansion using a composition described herein, for example a PDMS mesh, is enhanced relative to cell expansion utilizing beads, for example Dynabeads™. For example, as described in Tables 1 and 2 as well as FIG. 6, three day data exhibits higher proliferative index on mesh compositions described herein relative to a control, Dynabeads™. In yet another aspect, a mesh substrate described herein exhibits a higher proliferative index and a lower cell divisional percentage relative to a control, for example, Dynabeads™. In yet a further aspect, a mesh substrate described herein exhibits a higher proliferative index and a higher cell divisional percentage relative to a control, for example, Dynabeads™.

In another aspect, a mesh substrate described herein exhibits an about 5%, about 10%, about 15%, about 20%, about 25%, about 50%, or about 100% higher proliferative index relative to a control, for example, Dynabeads™. In yet another aspect, a mesh substrate described herein exhibits about 5%, about 10%, about 15%, about 20%, about 25%, about 50%, or about 100% higher proliferative index and a lower cell divisional percentage relative to a control, for example, Dynabeads™. In another aspect, the higher proliferative index is relative to Dynabeads™ M-280, M-450, and M-500.

In one aspect, a mesh substrate described herein provides for increased surface area and/or area to volume ratio as compared to Dynabeads™. In another aspect, a mesh substrate described herein provides for increased surface area and/or area to volume ratio as compared to Dynabeads™ which also improves the ability to increase cell expansion relative to a non-mesh substrate, for example, Dynabeads™.

In an aspect, cell expansion, for example T-cell or Stem cell on a mesh substrate comprising polydimethylsiloxane and polycaprolactone is improved by about 10%, about 20%, about 30%, about 40%, about 50%, about 60%, or about 75% relative to polycaprolactone alone. In another aspect, cell expansion, for example T-cell or Stem cell on a mesh substrate comprising polydimethylsiloxane and polycaprolactone is improved by at least about 10%, at least about 20%, at least about 30%, at least about 40%, at least about 50%, at least about 60%, or at least about 75% relative to polycaprolactone alone. In another aspect, cell expansion, for example T-cell or Stem cell on a mesh substrate comprising polydimethylsiloxane and polycaprolactone is improved by about 10% to about 75%, about 10% to about 30%, about 20% to about 50%, about 30% to about 50% relative to polycaprolactone alone. In another aspect, the improvement is measured by obtaining a higher proliferative index.

In one aspect, the present invention provides a method of stimulating cells, for example, T cells in culture, wherein the method includes culturing cells, for example, T cells in the presence of a biocompatible substrate with tunable rigidity. In an aspect, the substrate displays on its surface a first agent that stimulates a TCR/CD3 complex-associated signal in T cells and a second agent that stimulates a CD28 accessory molecule on the surface of T cells. In one embodiment, the first agent is an anti-CD3 antibody. In one embodiment, the second agent is an anti-CD28 antibody.

In one embodiment, the substrate also includes a co-stimulatory molecule selected from the group consisting of CD80, CD86, 4-1BBL, OX40L, ICOS-L, ICAM, PD-L1 and PD-L2.

The disclosure also provides a system and method for culturing and expanding cells, for example, T cells and stem cells. The method includes expanding cells using a biocompatible polymer substrate whereby the activation and expansion of the cells can be regulated by manipulating the stiffness of the substrate. Accordingly, the present invention allows for expansion of any cell, for example T cell and stem cell populations, and substantially increasing the number of cells, for example, T cells and stem cells, for subsequent use following expansion.

In one embodiment, the rigidity of the substrate can be manipulated to effect cell differentiation, for example, T-cell and stem cell differentiation.

Figure 3:
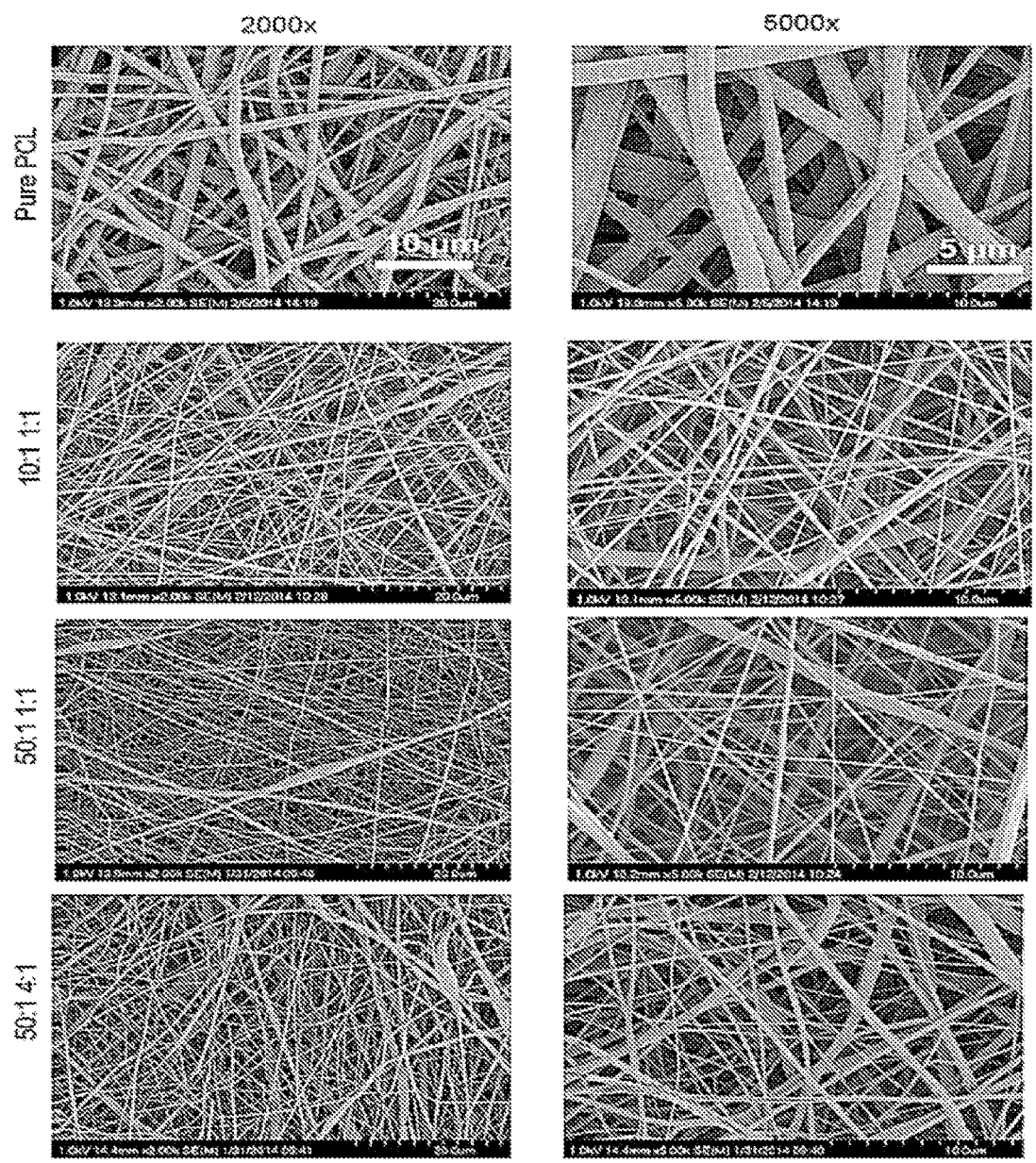
FIG. 3 sets forth mesh spun from 1:10 PDMS-A in 1:1 and 4:1 ratios with PCL.

In an aspect, substrate described herein comprises a mesh. In an aspect, substrate described herein comprises an electrospun mesh, for example, a mesh described herein in FIG. 3. In an aspect, the substrate described herein comprises a mesh form with a diameter of about 1-1000 μm, diameter of about 1-100 μm, and diameter of about 1-10 μm. In another example, the use of meshes with diameter greater than 1000 um promoted 10-20% greater growth than those in the 300-700 nm diameter range.

In an aspect, the substrate described herein comprises a natural polymer, biological polymer, synthetic polymer, or a combination thereof. In various embodiments, the polymer fibers used to create the substrate mesh described herein are selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides, aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

In another aspect, the disclosure provides for a substrate comprising a synthetic polymer or copolymer prepared from at least one of the group of monomers consisting of acrylic acid, methacrylic acid, ethyleneimine, crotonic acid, acrylamide, ethyl acrylate, methyl methacrylate, 2-hydroxyethyl methacrylate, lactic acid, glycolic acid, .ε-caprolactone, acrolein, cyanoacrylate, bisphenol A, epichlorhydrin, fry droxy alky lacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethyl methacrylate, vinyl pyridine, aminoethyl methacrylates, 2-methacryloyloxy-trimethylammonium chloride, N,N'-methylenebisacrylamide-, ethylene glycol dimethacrylates, 2,2'-(p-phenylenedioxy)-diethyl dimethacrylate, divinylbenzene, triallylamine, methylenebis-(4-phenyl-isocyanate), and polydimethylsiloxane elastomer (PDMS).

In an aspect, the substrate and component compositions can be altered or modified based on the optimization of rigidity. In an aspect, the description provides for compositions and methods comprising SYLGARD 184 ("PDMS-A-hard") (Dow Corning). In an aspect, the disclosure provides for polydimethylsiloxane or PDMS in a ratio of 1:10 of curing agent to base (for example, "PDMS-A-hard"). In another aspect, the bulk rigidity of polydimethylsiloxan, for example PDMS-A-hard, is about 1 MPa, 2 MPa, 3 MPa, or 4 MPa. In yet another aspect, the disclosure provides for polydimethylsiloxane in a ratio of about 1:50 of curing agent to base (for example, "PDMS-A-soft"). In an aspect, the bulk rigidity of polydimethylsiloxan, for example PDMS-A-soft, is about 20 kPa, 25 kPa, or 30 kPa.

In an aspect, the description provides for a NuSil med formulation 4086 ("PDMS-B"). In an aspect, the bulk rigidity of polydimethylsiloxan, for example PDMS-B, is about 40 kPa, 45 kPa, or 50 kPa. In an aspect, NuSil 486 comprises about a 1:1, about a 2.5:1, or about a 3:1 PDMS:PCL ratio.

In an aspect, the compositions described herein, for example, mesh compositions, exhibit a bulk rigidity of from about 20 kPa to about 75 kPa, from about 10 kPa to about 50 kPa, from about 20 kPa to about 40 kPa, from about 0.5 MPa to about 10 MPa, from about 1 MPa to about 5 MPa, and from about 2 MPa to about 4 MPa.

In another aspect, the disclosure provides for a synthetic nanofiber substrate comprising PDMS and poly(ε-caprolactone) for testing the effects of mechanical cues on cell behavior without interference from biological and/or chemical cues. The disclosure further provides for a method of testing the effects of mechanical cues on cell behavior without interference from biological and/or chemical cues by utilizing a substrate described herein, for example, a substrate comprising PDMS and poly(ε-caprolactone). In an aspect, the substrate composition, for example, the PDMS and poly(ε-caprolactone) substrate composition, allows for the independent modulation and study of physical matrix properties on cell behavior without the influence of biological and chemical variables on cell response.

In another aspect, the disclosure provides for a substrate comprising poly(ε-caprolactone) and another material capable of "softening" the surface of the substrate. In an aspect, the disclosure provides for a substrate comprising poly(ε-caprolactone) and an addition material when combined with poly(ε-caprolactone) to form a substrate is achieves or is capable of achieving a Young's Modulus "E" of less than about 100 kPa, E of less than about 75 kPa, or E of less than about 50 kPa.

In yet another aspect, the disclosure provides for a platform and/or method for diagnosing, evaluating, or studying the effects of physical environmental cues on cell behavior, such as matrix rigidity and nano-/micro-level geometry, by utilizing a substrate described herein. The disclosure further provides for a platform and/or method for diagnosing, evaluating, or studying the effects of physical environmental cues on cell behavior according to the methodology described in Example 7.

Sources of T Cells

Prior to expansion, a source of T cells can be obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

Enrichment of a cell population, for example T cell or stem cell population, by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4$^|$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4$^+$, CD25$^+$, CD62L$^{hi}$, GITR$^+$, and FoxP3$^+$.

In a further embodiment of the present invention, cells, for example, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoetic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Culture System

In an aspect, the methods of the present invention use agents/ligands bound to a surface to culture T cells. The surface may be any surface capable of having an agent/ligand bound thereto or integrated into and that is biocompatible, that is, substantially non-toxic to the target cells to be stimulated. The biocompatible surface may be biodegradable or non-biodegradable. The surface may be natural or synthetic, and a synthetic surface may be a polymer. The surface of the biocompatible substance of the invention represents a material with a bulk modulus that can be controlled by changing the ratio of base elastomer to curing agent.

An agent may be attached or coupled to, or integrated into a surface by a variety of methods known and available in the art. The agent may be a natural ligand, a protein ligand, or a synthetic ligand. The attachment may be covalent or noncovalent, electrostatic, or hydrophobic and may be accomplished by a variety of attachment means, including for example, chemical, mechanical, enzymatic, electrostatic, or other means whereby a ligand is capable of stimulating the cells. For example, the antibody to a ligand first may be attached to a surface, or avidin or streptavidin may be attached to the surface for binding to a biotinylated ligand. The antibody to the ligand may be attached to the surface via an anti-idiotype antibody. Another example includes using protein A or protein G, or other non-specific antibody binding molecules, attached to surfaces to bind an antibody. Alternatively, the ligand may be attached to the surface by chemical means, such as cross-linking to the surface, using commercially available cross-linking reagents (Pierce, Rockford, Ill.) or other means. In certain embodiments, the ligands are covalently bound to the surface.

In one aspect, the agent, such as certain ligands may be of singular origin or multiple origins and may be antibodies or fragments thereof while in another aspect, when utilizing T cells, the co-stimulatory ligand is a B7 molecule (e.g., B7-1, B7-2). These ligands are coupled to the surface by any of the different attachment means discussed above. The B7 molecule to be coupled to the surface may be isolated from a cell expressing the co-stimulatory molecule, or obtained using standard recombinant DNA technology and expression systems that allow for production and isolation of the co-stimulatory molecule(s) as described herein. Fragments, mutants, or variants of a B7 molecule that retain the capability to trigger a co-stimulatory signal in T cells when coupled to the surface of a cell can also be used. Furthermore, one of ordinary skill in the art will recognize that any ligand useful in the activation and induction of proliferation of a subset of T cells may also be immobilized on the surface of the biocompatible substance of the invention. In addition, while covalent binding of the ligand to the surface is one preferred methodology, adsorption or capture by a secondary monoclonal antibody may also be used. The amount of a particular ligand attached to a surface may be readily determined by flow cytometric analysis if the surface is that of beads or determined by enzyme-linked immunosorbent assay (ELISA) if the surface is a tissue culture dish, mesh, fibers, bags, for example.

In a particular embodiment, the stimulatory form of a B7 molecule or an anti-CD28 antibody or fragment thereof is attached to the same solid phase surface as the agent that stimulates the TCR/CD3 complex, such as an anti-CD3 antibody. In an additional embodiment, the stimulatory form of a 4-1BB molecule or an anti-4-lBB antibody or fragment thereof is attached to the same solid phase surface as the agent that stimulates the TCR/CD3 complex, such as an anti-CD3 antibody. In addition to anti-CD3 antibodies, other antibodies that bind to receptors that mimic antigen signals may be used. For example, surfaces of the invention may be coated with combinations of anti-CD2 antibodies and a B7 molecule and in particular anti-CD3 antibodies and anti-CD28 antibodies. In further embodiments, the surfaces may be coated with three or more agents, such as combinations of any of the agents described herein, for example, anti-CD3 antibodies, anti-CD28 antibodies, and anti-4-lBB antibodies.

Expansion of T Cells

The present invention further comprises a method of multiplying, expanding or otherwise culturing a T cell isolated using the methods disclosed herein or methods generally known in the art. Following isolation, a T cell is incubated in cell medium in a culture apparatus for a period of time or until the cells reach confluency before passing the cells to another culture apparatus. The culturing apparatus can be of any culture apparatus commonly used for culturing cells in vitro. Preferably, the level of confluence is greater than 70% before passing the cells to another culture apparatus. More preferably, the level of confluence is greater than 90%. A period of time can be any time suitable for the culture of cells in vitro. T cell medium may be replaced during the culture of the T cells at any time. Preferably, the T cell medium is replaced about every 2 to 3 days. T cells are then harvested from the culture apparatus whereupon the T cells can be used immediately or cryopreserved to be stored for use at a later time. T cells may be harvested by trypsinization, EDTA treatment, or any other procedure used to harvest cells from a culture apparatus. In an aspect, cell density can be measured every few days, for example, 1, 2, 3, 4, or 5 days or more, but media can be added continuously. In an aspect, compositions and methods described herein are used in conjunction with a bioreactor, such as the WAVE bioreactor (GE Healthcare Life Sciences).

In one embodiment of the invention, the T cells may be stimulated by a single agent. In another embodiment, T cells are stimulated with two agents, one that induces a primary signal and a second that is a co-stimulatory signal. Ligands useful for stimulating a single signal or stimulating a primary signal and an accessory molecule that stimulates a second signal may be used in soluble form, attached to the surface of a cell or immobilized on a surface as described herein. In a preferred embodiment both primary and secondary agents are co-immobilized on a surface, for example a bead or an artificial presenting cell (aAPC). In one embodiment, the molecule providing the primary activation signal, such as a CD3 ligand, and the co-stimulatory molecule, such as a CD28 ligand are coupled to or loaded on the same surface, for example, a particle or an aAPC.

The medium used to multiply the T cells of the present invention comprises an agent that can stimulate CD3 and CD28 on the T cell. For example, an agent that can stimulate CD3 is an antibody to CD3, and an agent that can stimulate CD28 is an antibody to CD28. Preferably, the agent is immobilized on a biocompatible substrate whose surface rigidity is selected to optimize cell expansion. This is because, as demonstrated by the data disclosed herein, and increase in overall culture yield is observed when comparing the softest substrate (1:50 cross-linker to base ratio) to the stiffest substrate (1:5 cross-linker to base ratio) tested.

Methods of Use and Pharmaceutical Compositions

Generally, the cells activated and expanded as described herein may be utilized in the treatment and prevention of various diseases. The present invention provides a platform for the ex vivo culture of T cells for adoptive immunotherapy with potential advantages over currently used rigid plastic surfaces or Dynabeads™.

Pharmaceutical compositions of the present invention may be administered in a manner appropriate to the disease to be treated. The quantity and frequency of administration will be determined by such factors as the condition of the patient, and the type and severity of the patient's disease, although appropriate dosages may be determined by clinical trials. The immune response induced in a subject by administering T cells activated and expanded using the methods described herein, or other methods known in the art wherein T cells are stimulated and expanded to therapeutic levels, may include cellular immune responses mediated by cytotoxic T cells, capable of killing tumor and infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Coligan et al. Current Protocols in Immunology, John Wiley & Sons Inc. (1994).

In certain embodiments, it may be desired to administer activated T cells to a subject and then subsequently redraw blood (or have a leukapheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

EXAMPLES

Example 1

Figure 4:
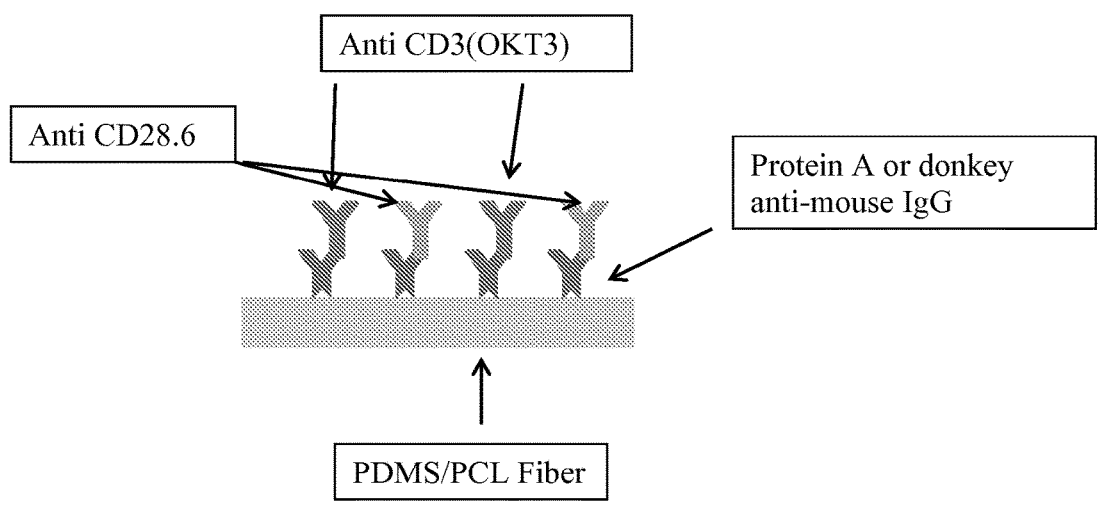
FIG. 4 sets forth a mesh coating procedure outlined in Example 1, where (A) includes a PDMS-A/PCL fiber, (B) includes intermediate proteins such as Protein A or donkey-anti-mouse IgG, (C) includes anti CD3 (OKT3), and (D) includes anti CD28.6.
Figure 5:
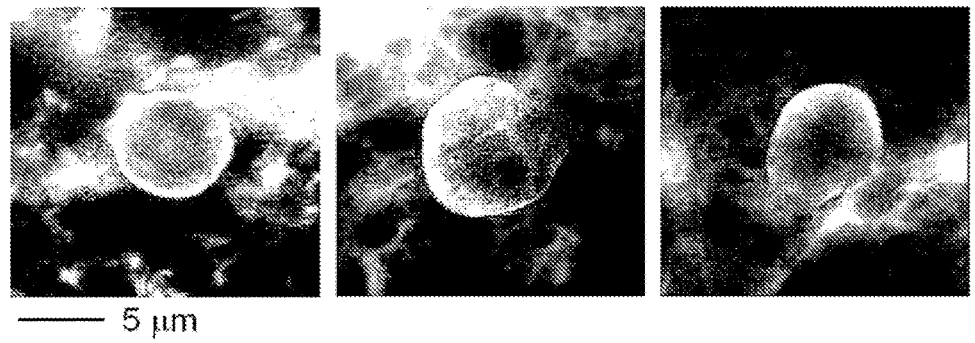
FIG. 5(A) provides for fluorescent protein adhesion indicating distinct fibrous scaffold and cell adhesion; (B) provides for a graph of cell proliferation as evaluated with a negative control (no stimulation), positive control (Dynabeads™), a 1:10 PDMS-A 4:1 PCL ratio, a 1:50 PDMS-A 1:1 PCL ratio, a 1:50 PDMS-A 4:1 PCL ratio, and a 1:10 PDMS-A 1:1 PCL ratio.
Figure 5:
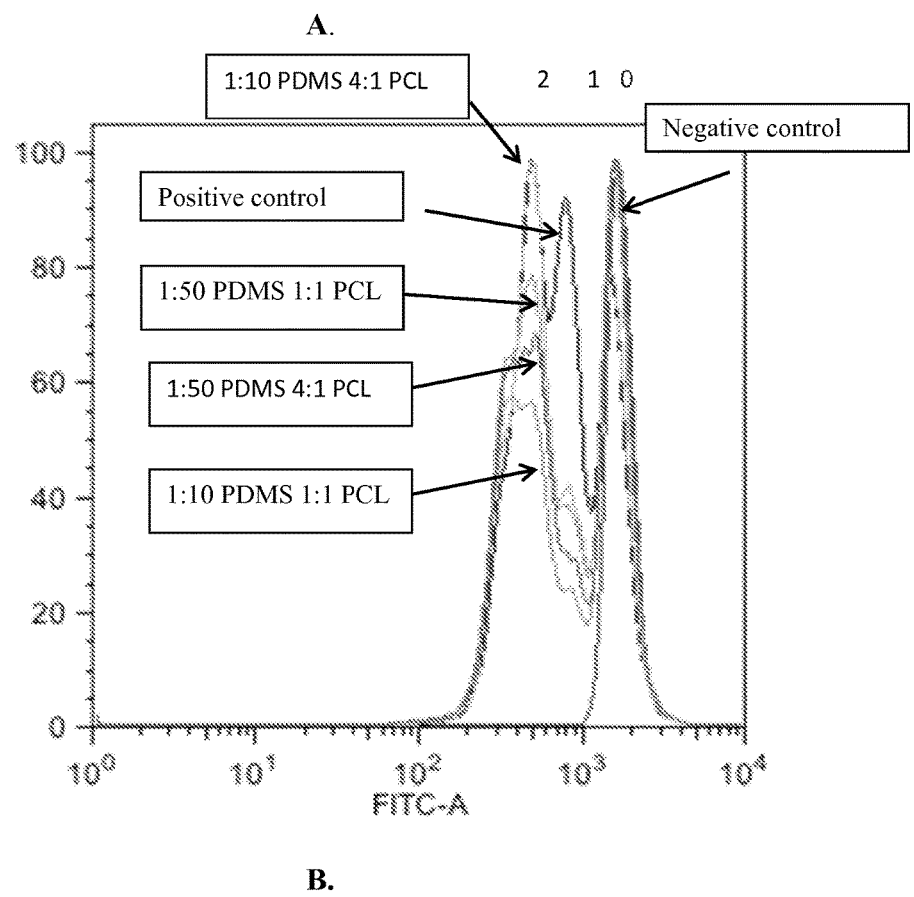
Figure 7:
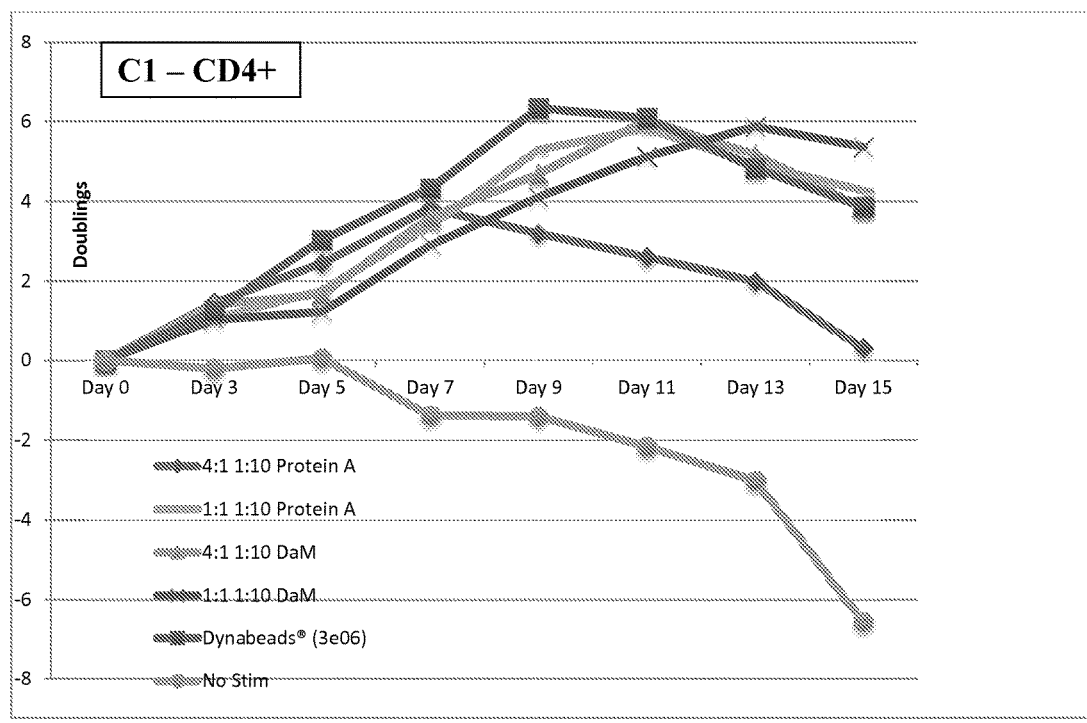
FIG. 7 provides for an image demonstrating CD4 cell expansion for a variety of PDMS-A and PCL ratios.
Figure 8:
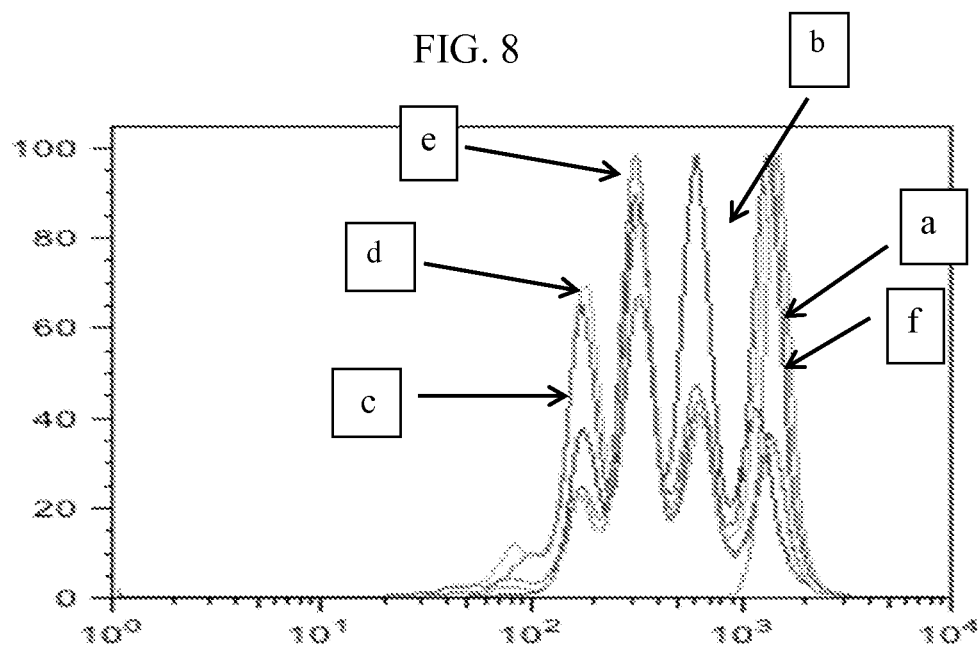
FIG. 8(A) provides for a graph of cell proliferation as evaluated with a negative control (no stimulation) ("a"), positive control (Dynabeads™ 3E06) ("b"), a 1:10 PDMS-A 4:1 PCL ratio (Protein A) ("c"), a 1:10 PDMS-A 1:1 PCL (Protein A) ratio ("d"), a 1:10 PDMS-A 4:1 PCL (Donkey anti-mouse) ratio ("e"), and a 1:10 PDMS 1:1 PCL (Donkey anti-mouse) ratio ("f") and (B) provides for a graph of cell proliferation as evaluated with a negative control (no stimulation) ("a"), positive control (Dynabeads™ 3E06) ("b"), a 1:10 PDMS-A 4:1 PCL ratio (Protein A) ("c"), a 1:10 PDMS-A 1:1 PCL (Protein A) ratio ("d"), a 1:10 PDMS-A 4:1 PCL (Donkey anti-mouse) ratio ("e"), and a 1:10 PDMS 1:1 PCL (Donkey anti-mouse) ratio (f").
Figure 8:
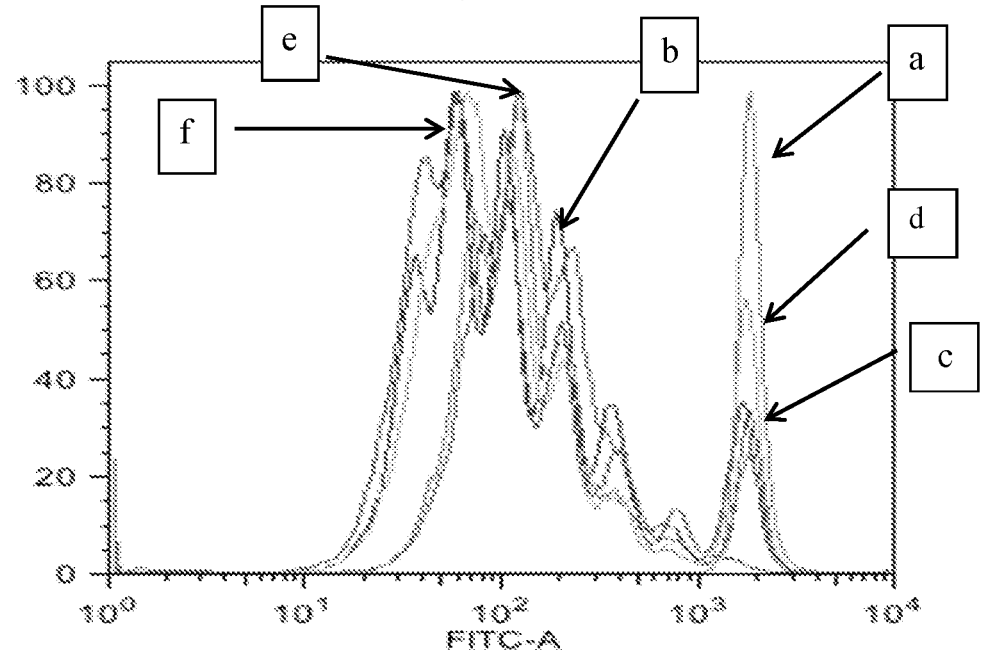
Figure 9:
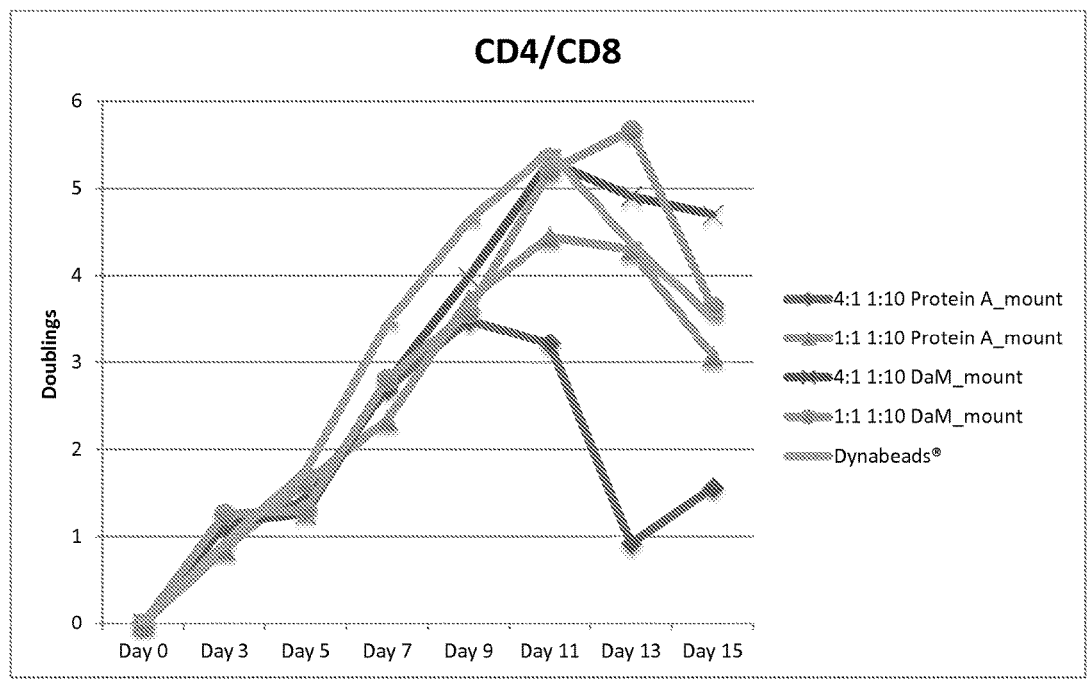
FIG. 9 provides for an image demonstrating CD4/CD8 cell expansion for a variety of PDMS-A and PCL ratios.
Figure 10:
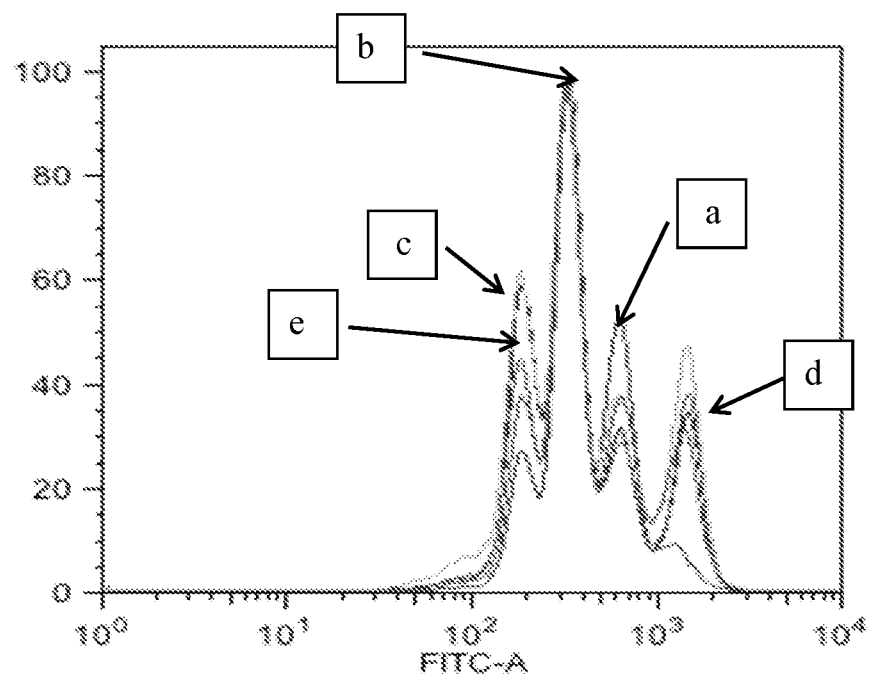
FIG. 10(A) provides for a graph of cell proliferation as evaluated with a positive control (Dynabeads™ 3E06) ("a"), a 1:10 PDMS-A 4:1 PCL ratio (Protein A) (b"), a 1:10 PDMS-A 1:1 PCL (Protein A) ratio, a 1:10 PDMS 4:1 PCL (Donkey anti-mouse) ratio, and a 1:10 PDMS-A 1:1 PCL (Donkey anti-mouse) ratio and (B) provides for a graph of cell proliferation as evaluated with a positive control (Dynabeads™ 3E06) ("a"), a 1:10 PDMS-A 4:1 PCL ratio (Protein A) ("b"), a 1:10 PDMS-A 1:1 PCL (Protein A) ratio ("c"), a 1:10 PDMS-A 4:1 PCL (Donkey anti-mouse) ratio ("d"), and a 1:10 PDMS-A 1:1 PCL (Donkey anti-mouse) ratio ("e").
Figure 10:
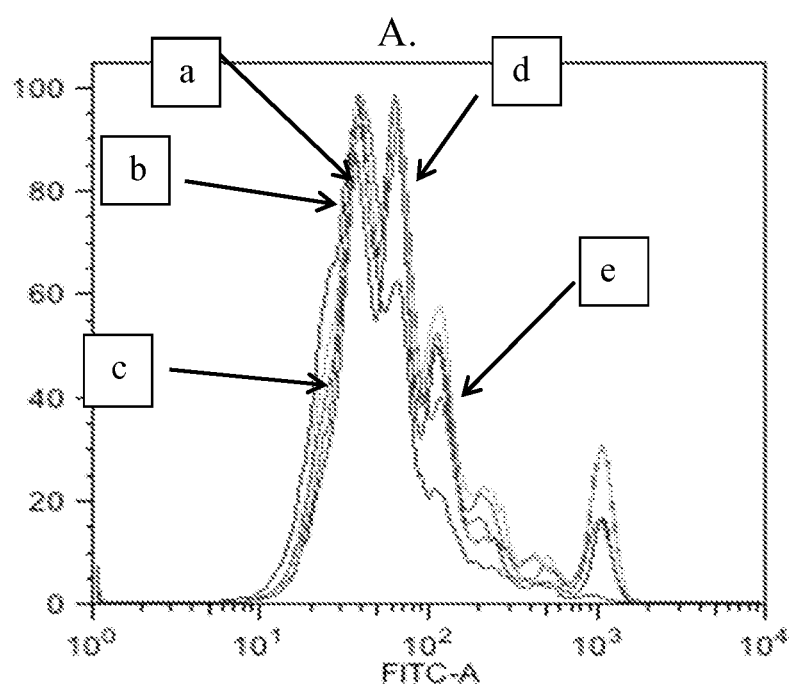

This example provides for a representative method for coating mesh substrates described herein by utilizing the following procedure:
(1) Mesh is treated with UV light for 30 minutes. O-rings are soaked in EtOH and treated under UV light for 30 minutes.
(2) O-rings are dried and used to secure mesh after it is peeled from foil.
(3) Setup is soaked in EtOH and treated with UV for 30 minutes.
(4) Mesh setup is dried completely before Protein A or Donkey-anti-mouse is applied for 2 hours at room temperature.
(5) Mesh is washed 3× with PBS and then incubated with a 4:1 mixture of OKT3 and CD28.6 for 2 hrs at room temp
(6) Mesh is washed 3× with PBS and cells (treated with CFSE) are seeded. See, for example, FIG. 4 attached herein.

Example 2

This example provides for cell expansion over a 15 day period utilizing an electrospun mesh substrate described herein.

As described in Tables 1 (CD4 cells) and 2 (CD4/CD8) and FIGS. 7-10, cells were expanded over 15 day period, with a three-day stimulation. Donkey-anti-mouse IgG (DaM) and Protein A served as linkers for OKT3/CD28 antibody presentation, respectively. CFSE dye is used for proliferation tracking over the first few days of growth. As described in Tables 1 and 2, electrospun mesh models incurred a greater number of divisions per cell, on average.

TABLE 1

| Day 3 | % Cell Divided | Prolif. Index |
| --- | --- | --- |
| 1:10 PDMS 4:1 with PCL (Protein A) | 32.7 | 1.69 |
| 1:10 PDMS 1:1 with PCL (Protein A) | 34.7 | 1.77 |
| 1:10 PDMS 4:1 with PCL (Donkey-anti-mouse) | 58.4 | 1.61 |
| 1:10 PDMS 1:1 PCL (Donkey-anti-mouse) | 58.8 | 1.58 |
| Positive control (Dynabeads ® 3E06) | 63.2 | 1.41 |
| Negative control (No stimulation) | 0 | 0 |

TABLE 2

| Day 3 | % Cells Divided | Prolif. Index |
| --- | --- | --- |
| 1:10 PDMS 4:1 with PCL (Protein A) | 59.3 | 1.7 |
| 1:10 PDMS 1:1 with PCL (Protein A) | 52.6 | 1.75 |
| 1:10 PDMS 4:1 with PCL (Donkey-anti-mouse) | 53.7 | 1.75 |
| 1:10 PDMS 1:1 PCL (Donkey-anti-mouse) | 58.2 | 1.81 |
| Control (Dynabeads ® 3E06) | 83.6 | 1.57 |

Example 3

This example evaluates the mechanical properties of electrospun mesh described herein.

Figure 11:
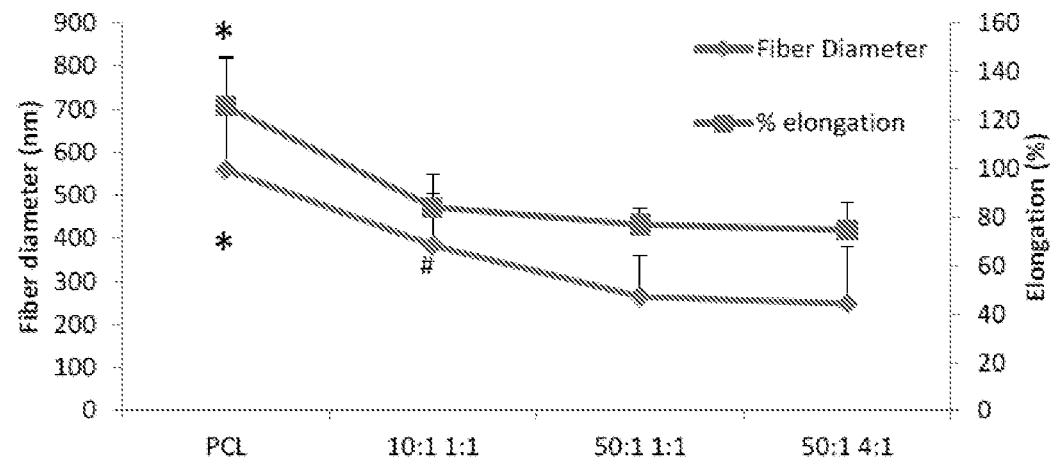
FIG. 11 sets forth fiber diameter, elongation percentage, and modulus for mesh substrates described herein prepared under various conditions.
Figure 11:
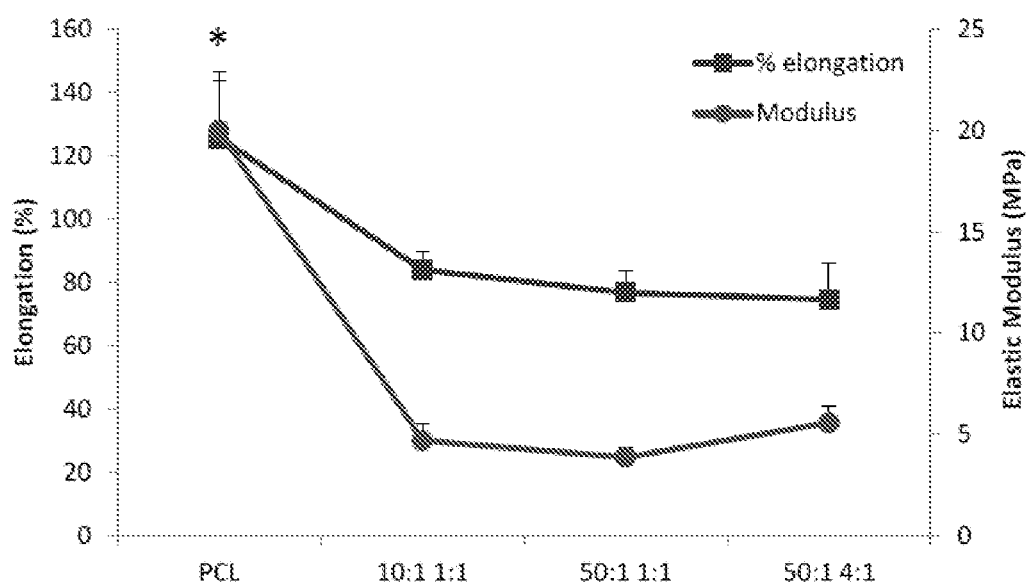

Samples of electrospun mesh described herein were tested to failure under uniaxial tension. Scaffolds (6 cm×1 cm, n=5/group) were secured using custom clamps and mounted on an Instron mechanical testing device with an average gauge length of 3 cm. Samples were evaluated at a strain rate of 5 mm/min and elongation and elastic modulus were calculated from the stress-strain curve. Fiber diameter, elongation percentage, and modulus for mesh substrates prepared under various conditions were evaluated in Table 3 and FIG. 11.

TABLE 3

| PDMS:Curing agent | PDMS:PCL | Fiber Diameter (nm) | Pore Size (μm) | UTS (MPa) | Elastic Modulus (MPa) |
|---|---|---|---|---|---|
| N/A | 0:4 | 559.50 ± 257.86* | 2.75 ± 0.45 | 4.31 ± 0.61 | 20.02 ± 2.44* |
| 10:1 | 1:1 | 383.38 ± 163.30# | 1.9 ± 0.46 | 4.55 ± 0.14 | 4.67 ± 0.80 |
| 10:1 | 4:1 | 293 ± 104 | 1.48 ± 0.79 | | |
| 50:1 | 1:1 | 264.58 ± 94.09 | 2.21 ± 0.38 | 3.52 ± 0.31 | 3.85 ± 0.45 |
| 50:1 | 4:1 | 248.52 ± 131.06 | 2.48 ± 0.52 | 4.98 ± 1.22 | 5.56 ± 0.86 |

Tensile testing exhibited rigid bulk properties (MPa). For example, PDMS added to PCL can result in a softer modulus and thinner fibers than PCL alone.

Example 4

This example sets forth Atomic Force Microscopy (AFM) measurements performed on electrospun mesh described herein.

Figure 12:
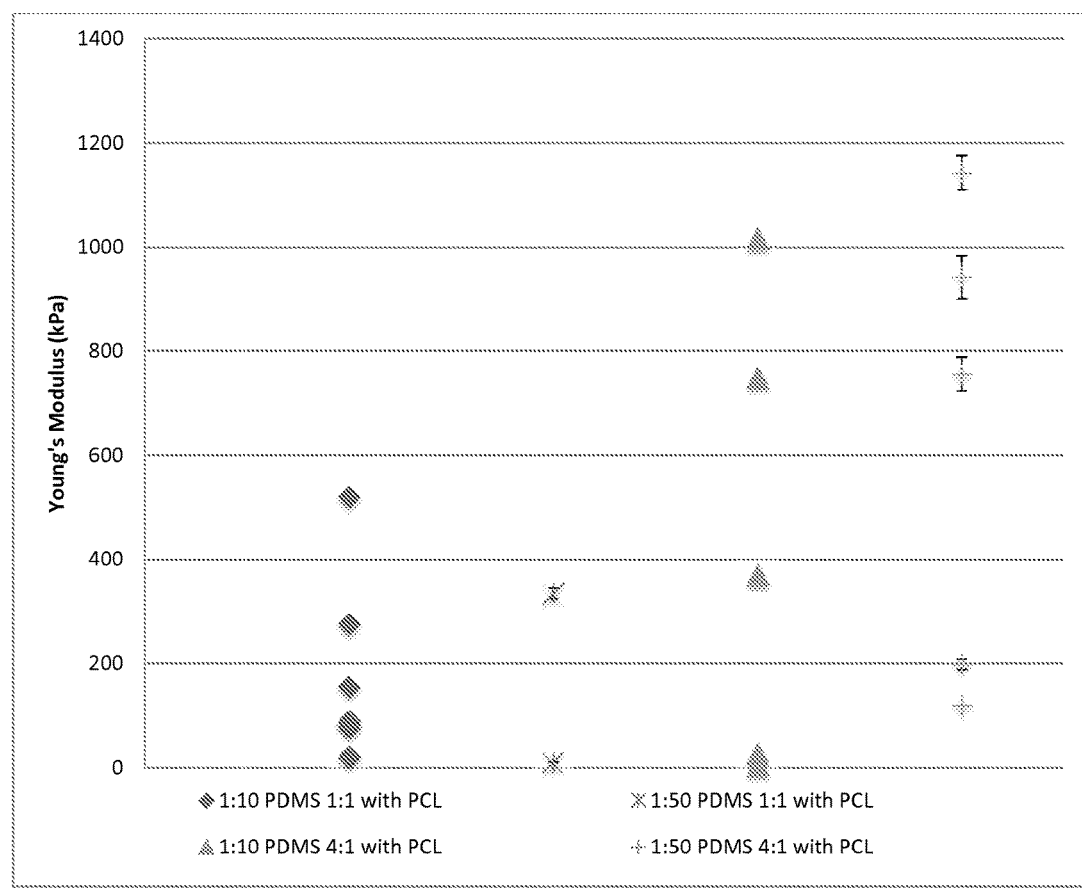
FIG. 12 provides for Atomic Force Microscopy images for mesh substrates described herein prepared under various conditions.
Figure 13:
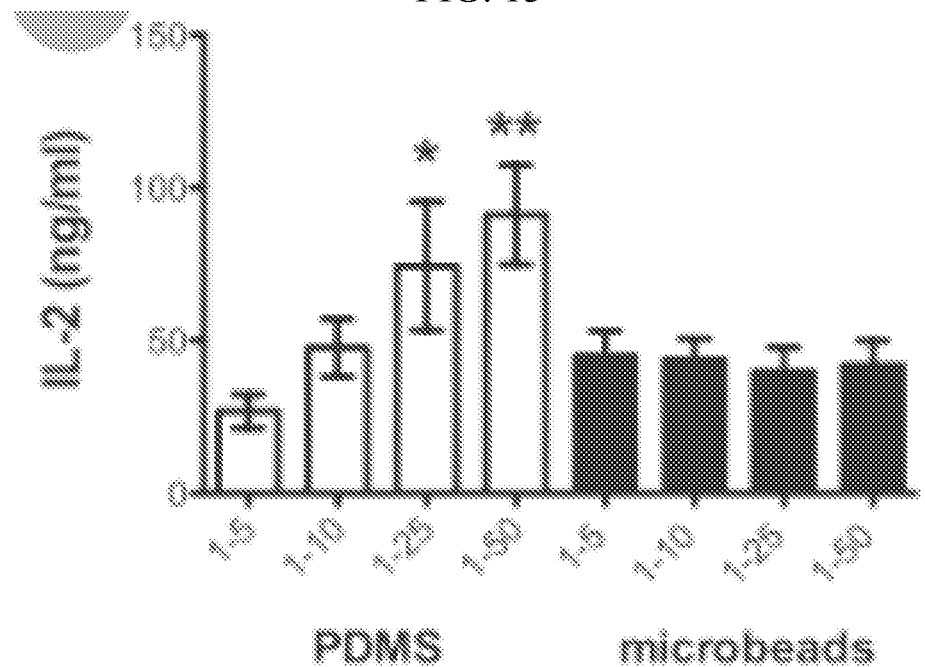
FIGS. 13(A) and (B) provides for an analysis of rigidity-dependent activation of CD4+ T cells. Three day IL-2 secretion and cell attachment correlate with Young's modulus. *P<0.05, **P<0.005 compared to 200 kPa surface.
Figure 13:
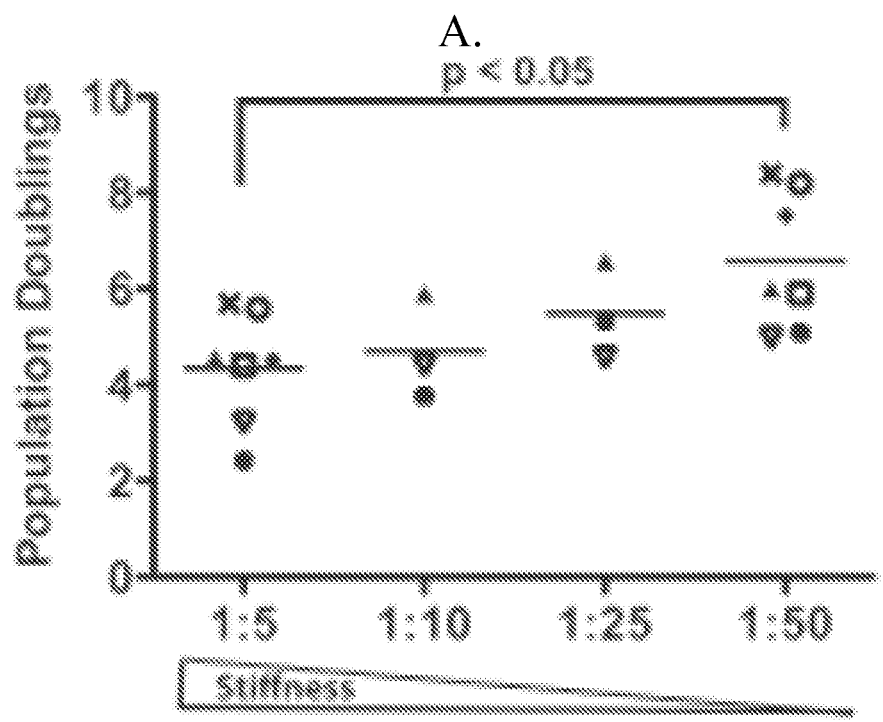

As described in FIG. 12, AFM measurements performed with a 4.5 um-diameter polystyrene tip, chosen to mimic cell-surface interaction showed soft (100 s of kPa) mesh, are spun from inherently stiffer bulk material (MPa).

Spun 4:1 PDMS:PCL measured twice as rigid as 1:1 at the local level. The difference in 4:1 PDMS:PCL (Mean=521.743, Var=179946.7) and 1:1 PDMS:PCL (Mean=174.241, Var=27098.82) was statistically significant t(40)=4.211, p<0.05, one-tailed and two-tailed.

Example 5

This example sets forth fibrous meshes that were formed via co-electrospinning of PDMS and poly(ε-caprolactone, MW=210 kDa) (PCL) in 3:1 v/v dicholoromethane (DCM)/ N,N-dimethylformamide (DMF) at 8-10 kV onto a horizontally rotating drum spinning at 2100 rpm for aligned fibers or onto a grounded collection plate for unaligned fibers. Horizontal working distances were maintained between 8 and 10 cm. Modulation of PDMS to PCL w/w ratio, PDMS formulation, and total polymer concentration allowed for the creation of a wide range of meshes.

PDMS:PCL w/w ratio: 1:1, 2.5:1, 3:1
PDMS formulation: Sylgard 184 elastomer/NuSil MED 4086 elastomer
Polymer concentration: 19, 35, 40, 45, and 50 wt. %

Figure 14:
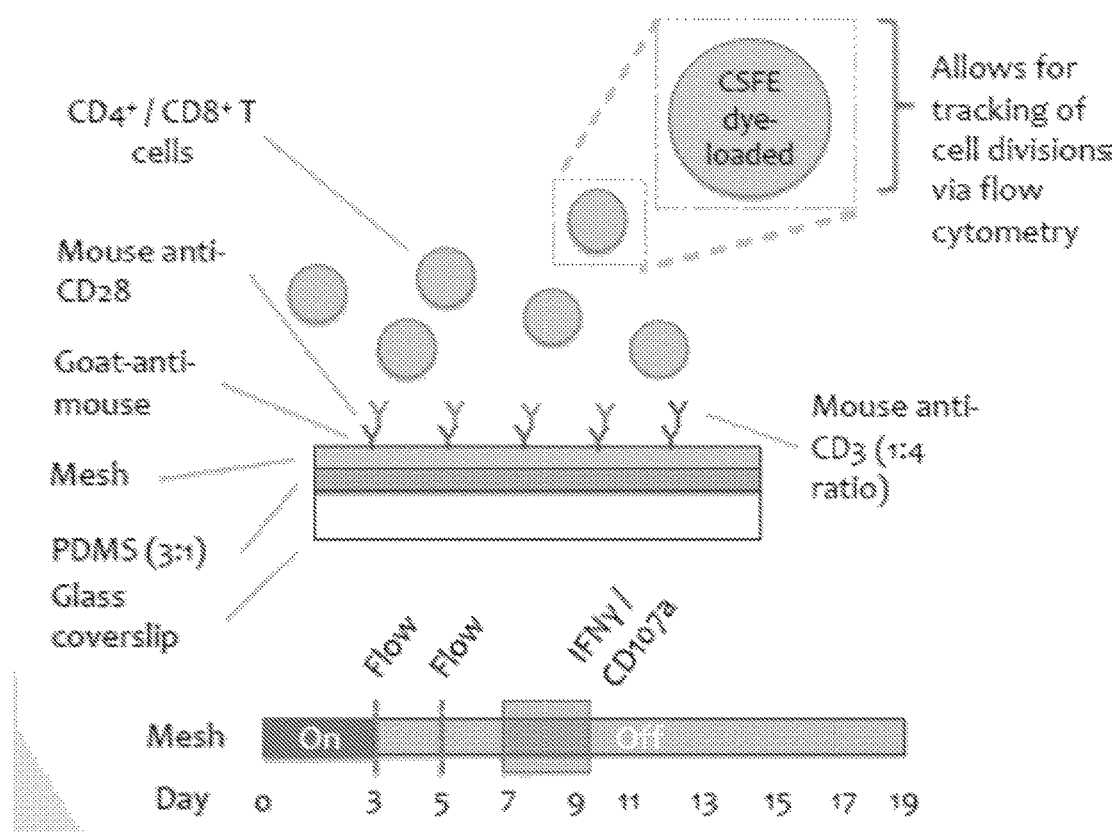
FIG. 14 provides for a cell proliferation schematic according to an aspect of the disclosure.
Figure 15:
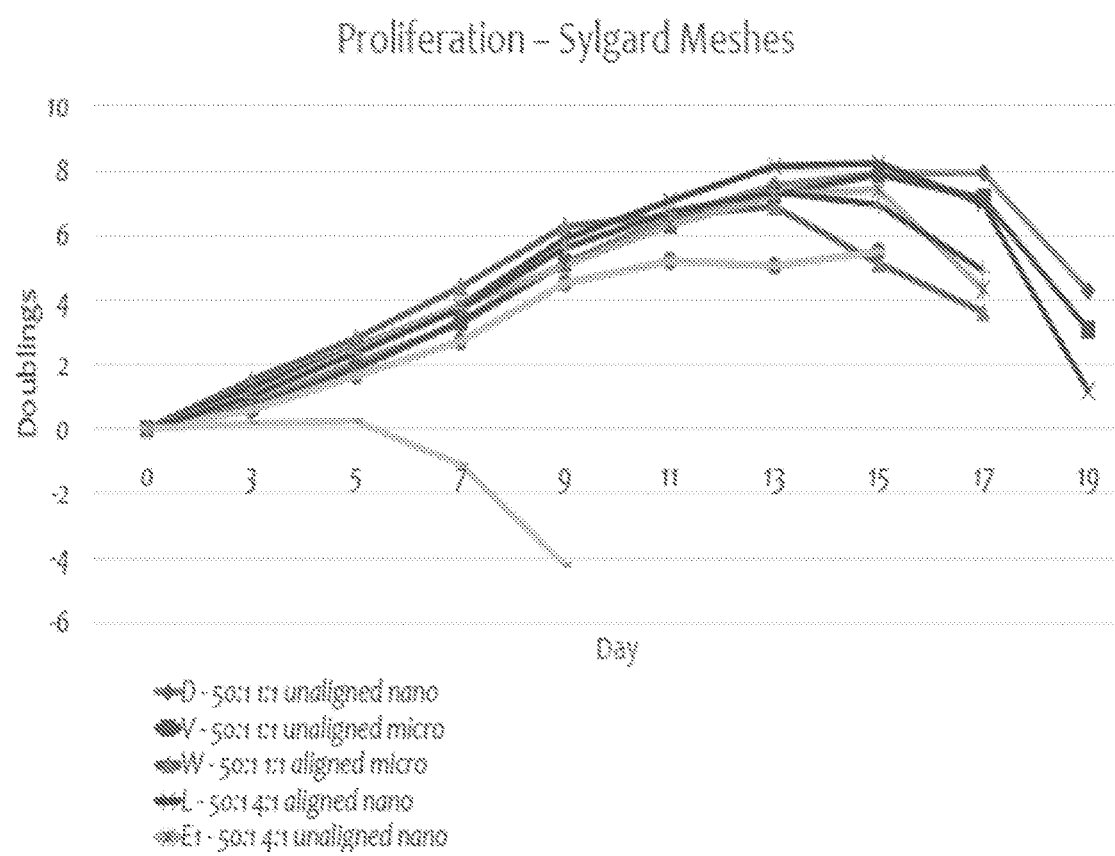
FIG. 15 provides for a graph of cell proliferation for SYLGARD 184 fiber mesh substrate under various conditions.

As described in FIG. 14, coating of meshes with activating antibody was done via direct adsorption of goat-anti-mouse IgG onto mesh surfaces (2 h, 23° C.) followed by linkage with a 1:4 ratio of mouse IgG-anti-human CD3 (OKT3) to mouse IgG-anti-human CD28 (9.3) (2 h, 23° C.). Cells were treated with fluorescein-isothiocyanate-tagged carboxy-fluorescein succinimidyl ester (FITC-CFSE) in order to track cell division and expansion.

Additionally, cell proliferation studies were performed using human CD4+/CD8− T cells isolated from healthy donors (NYBC) via Rosette Sep Human T Cell Enrichment Cocktail (StemCell Technologies). Cells were monitored for up to 19 days with counting every other day starting from day 3. In addition, flow cytometry was performed on days 3 and 5, along with activity assays for IFN-γ and CD107 on day 7.

Example 6

Figure 17:
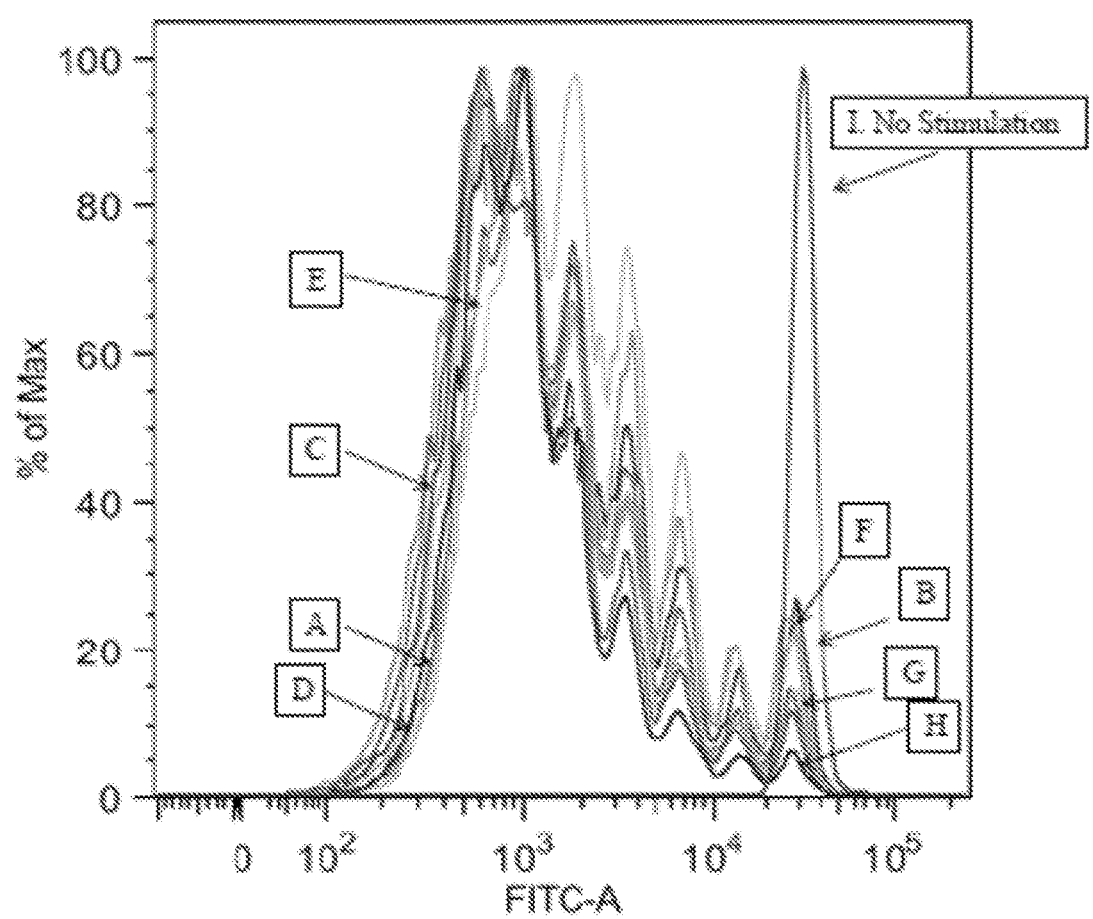
FIG. 17 provides for a graph of cell proliferation under the conditions specified in FIG. 16 for SYLGARD 184 fiber mesh substrate.

This example sets forth proliferation on Sylgard 184 fiber mesh for long-term culture for 19 days coupled with approximately 8 max doublings for experimental meshes indicated a robust system for expansion of T cells. Flow cytometry (BD FACS Canto II) revealed proliferation indices comparable or significantly higher than that of the current gold standard and pure PCL controls as described in FIGS. 15-17.

Figure 18:
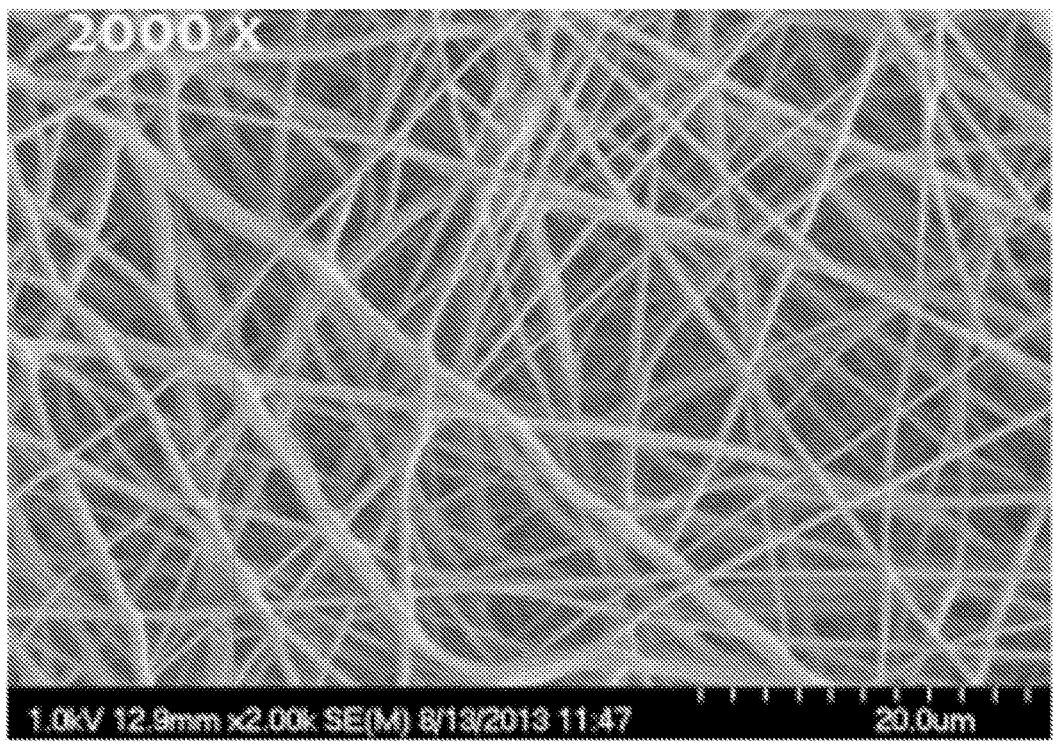
FIG. 18(A) provides for Atomic Force Microscopy images for SYLGARD 184 fiber mesh substrate; (B) provides for analysis of fiber diameter, bulk elastic modulus, and (C) local elastic modulus.
Figure 19:
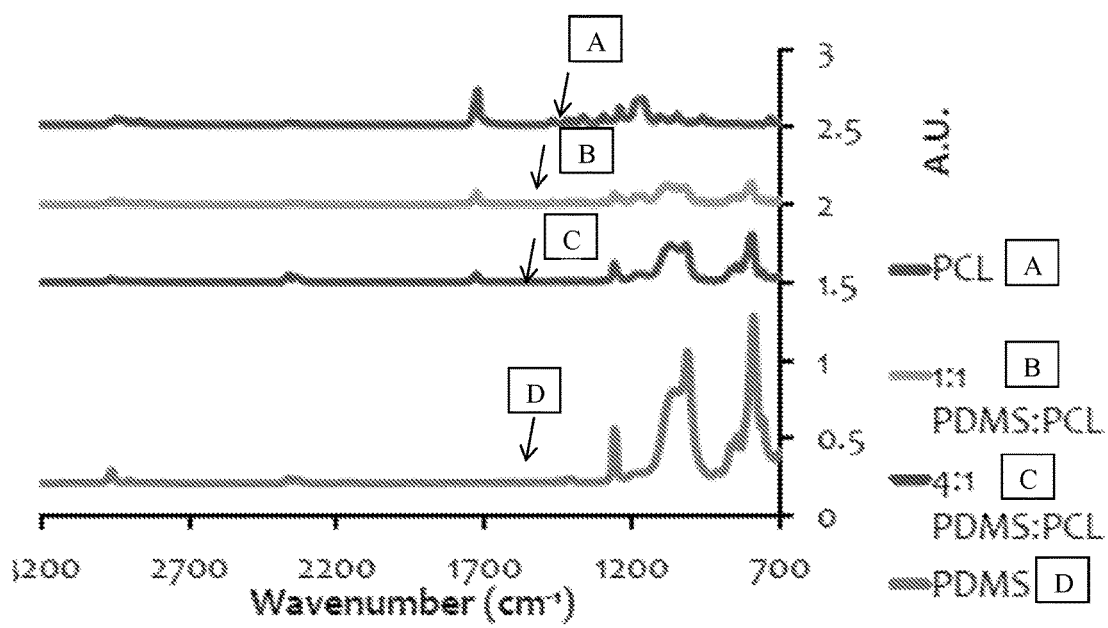
FIG. 19 provides for a graph analyzing wavenumber for (A) PCL, (B) 1:1 PDMS:PCL, (3) 4:1 PDMS:PCL, and (4) PDMS.
Figure 20:
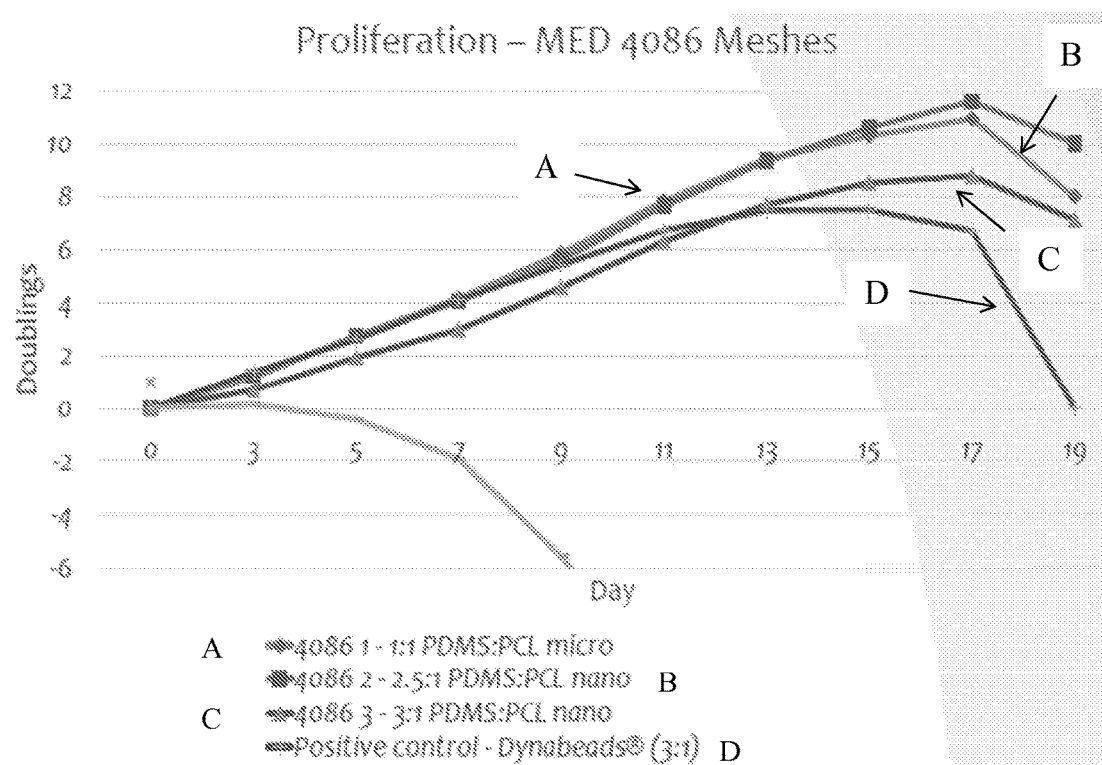
FIG. 20 provides for a graph of proliferation on NuSil MED 4086 fiber under various conditions.
Figure 21:
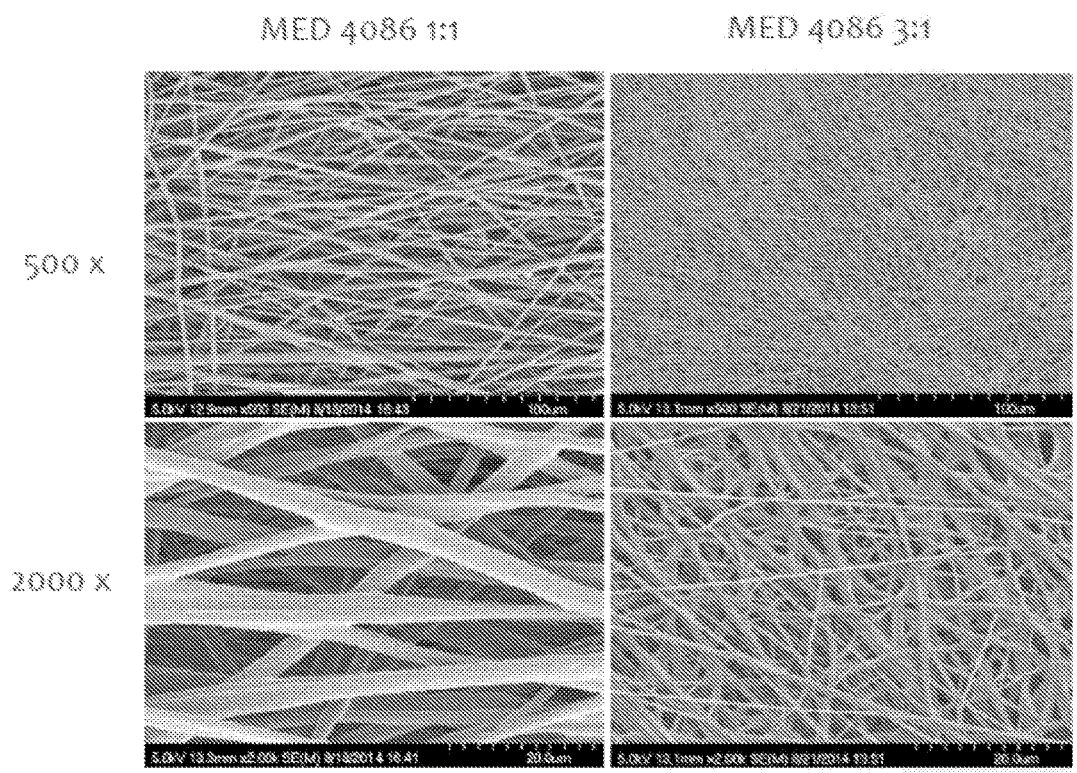
FIG. 21 provides for Atomic Force Microscopy images for mesh substrates described herein for a NuSil MED 4086 fiber substrate with a 1:1 PDMS:PCL micro ratio and a 3:1 PDMS:PCL nano ratio.
Figure 22:
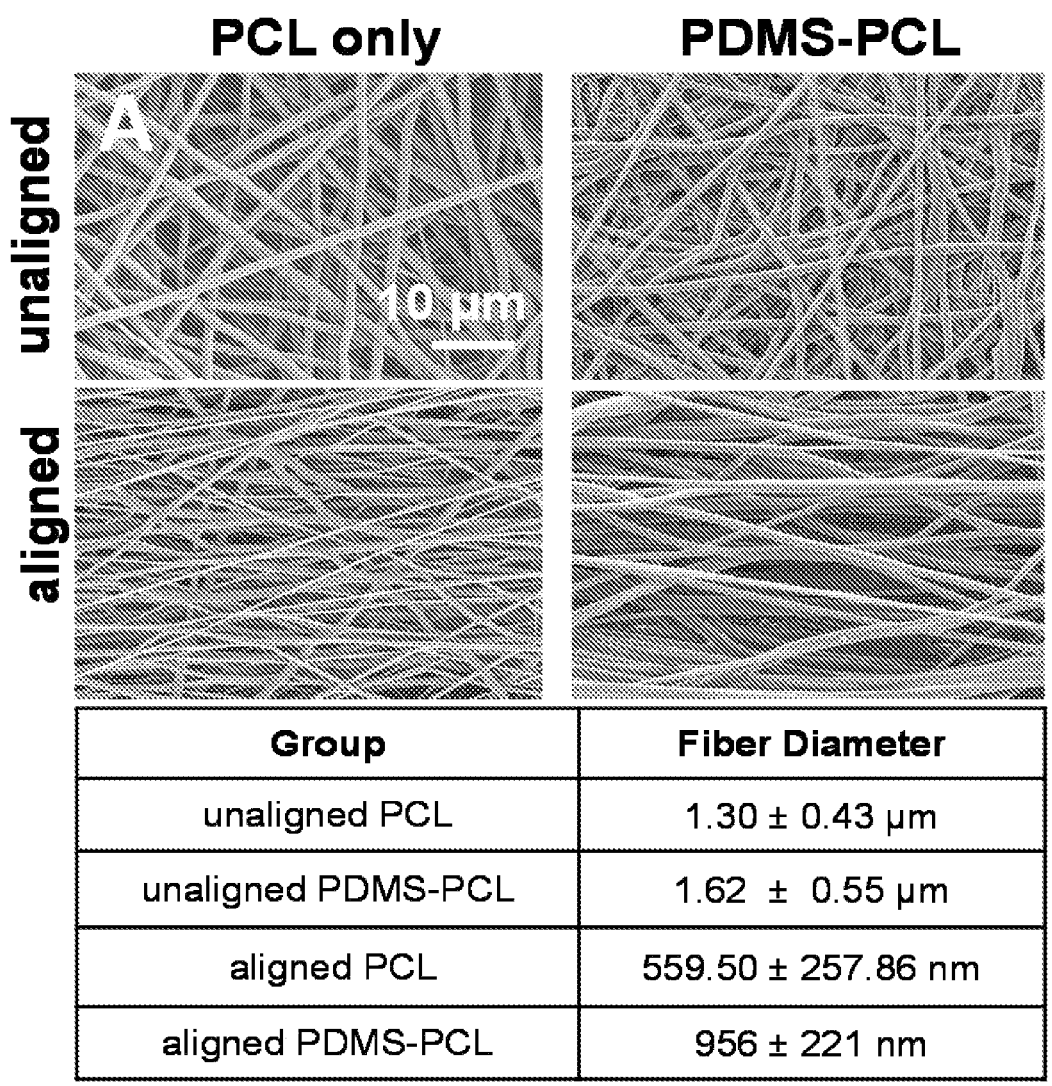
FIG. 22 provides for SEM and associated fiber diameter analysis of unaligned and aligned PCL and PDMS-PCL meshes (n=2).

Analysis via FTIR revealed proper incorporation and uniform dispersion of PDMS and PCL components. Material properties were assessed through tensile testing and morphology investigated via scanning electron microscopy (SEM). Atomic force microscopy (AFM) indentation measurements were conducted with a 4.5 μm ball tip to examine rigidities perceived on the cellular level. As set forth in FIG. 18, electrospun mesh with nano-scale fibers exhibit softer local rigidities, as compared to its bulk properties.

Example 7

This example describes a platform for evaluating stem cell behavior.

Nanofiber Fabrication:

Unaligned and aligned meshes composed of either a 1:1 blend of PDMS (Sylgard 184; Dow Corning) and PCL (Sigma-Aldrich) or PCL only were formed via electrospinning. The PDMS-PCL samples were then left to cure overnight at room temperature to allow for PDMS crosslinking.

Characterization:

Qualitative analysis of fiber morphology, alignment, diameter and pore size were performed using scanning electron microscopy (SEM; Hitachi, n=2). Scaffold composition was also performed using Fourier Transform Infrared (FTIR) imaging (n=2).

Mechanical Testing:

Elastic modulus, ultimate tensile strength, and % elongation for each polymer blend were tested via uniaxial tensile testing at a strain rate of 5 mm/min (Instron, n=6).

Cell Seeding:

Scaffolds were seeded with human MSC (21 y/o M; Lonza) at $3 \times 10^4$ cells/cm$^2$ and cell response was analyzed on days 1, 7, and 21.

End-Point Analyses:

Cell viability and morphology (n=2) were examined by Live/Dead assay and cell proliferation and fold change in cell number (n=5) were assessed by PicoGreen dsDNA assay.

Statistical Analysis:

Results are presented in the form of mean±standard deviation, with n equal to the number of samples per group. ANOVA and the Tukey-Kramer post-hoc test were used for all pair-wise comparisons (*p<0.05).

Figure 23:
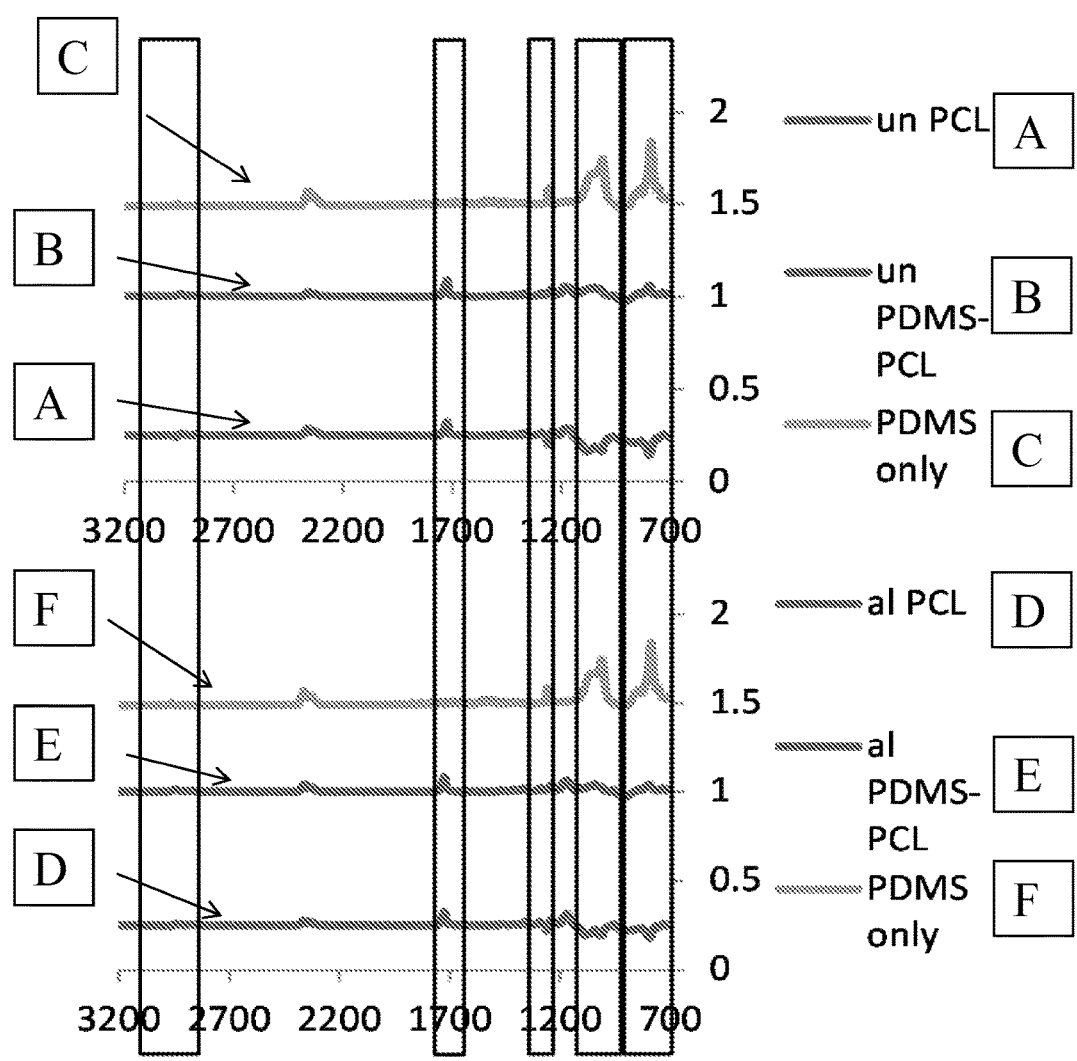
FIG. 23 provides for FTIR data confirming the presence of PDMS and PCL in nanofiber meshes (n=2).

Nanofiber Characterization:

SEM revealed that fibers in all meshes were uniform, with fiber diameters on the order of one micron, except for aligned PCL scaffolds, which exhibited a lower fiber diameter. FTIR data confirms that both PDMS and PCL chemical groups were incorporated into PDMS-PCL fibers (FIG. 23).

Figure 24:
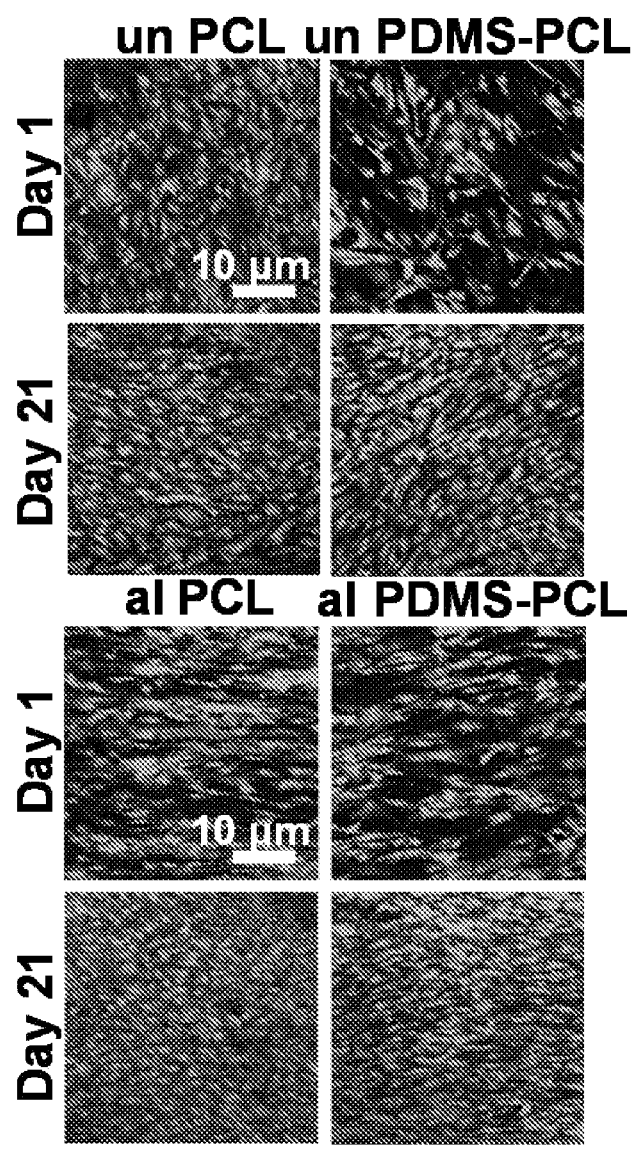
FIG. 24 provides for Live/Dead images of hMSC seeded on unaligned and aligned PCL and PDMS-PCL meshes after 1 and 21 days in vitro (n=2).
Figure 25:
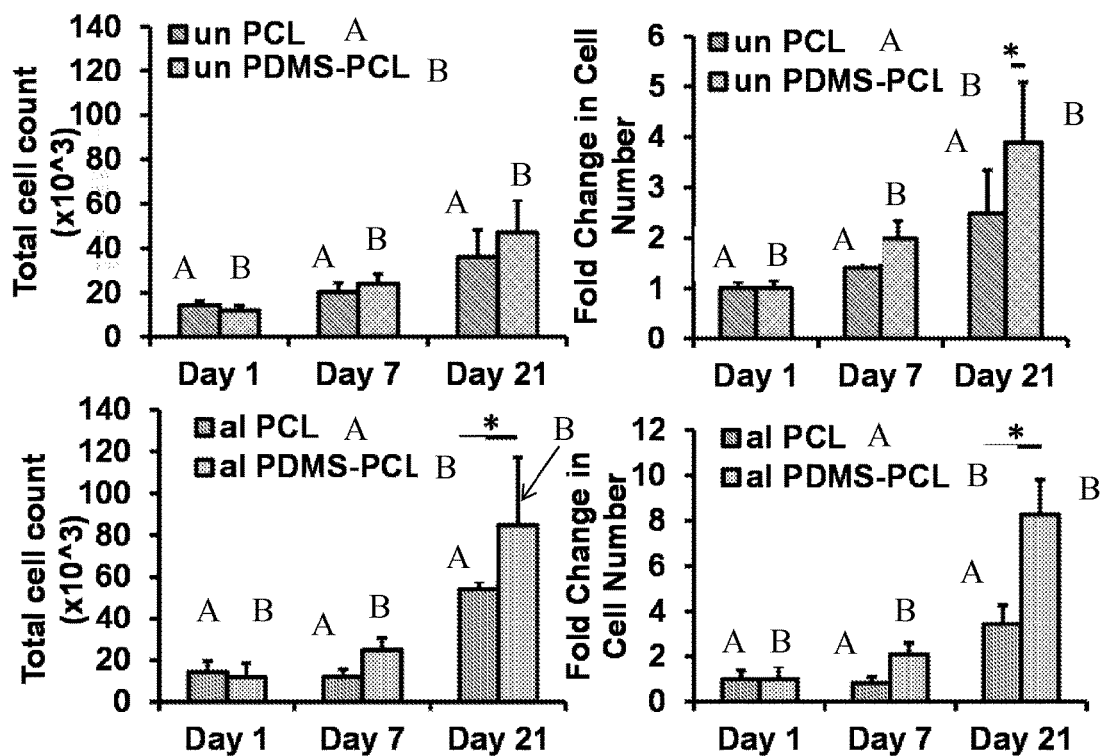
FIG. 25 indicates that fold change in stem cell number was significantly greater for PDMS-PCL scaffolds after 21 days compared to PCL scaffolds regardless of alignment (n=5).

Cell Viability and Proliferation:

Cells remain viable in all groups over time (FIGS. 24 and 25). Cell number on both PDMS-PCL and PCL scaffolds increased significantly by day 21, regardless of alignment. For unaligned scaffolds, fold change in cell number was significantly greater on PDMS-PCL scaffolds compared to PCL scaffolds on day 21. For aligned scaffolds, both total cell number and fold change in cell number were significantly greater on PDMS-PCL scaffolds when compared to PCL scaffolds (FIGS. 24 and 25).

Proliferation data shows that MSC growth rate is increased on the PDMS-containing scaffolds, when compared to PCL alone. A similar trend was seen for both aligned and unaligned fibers. These differences likely arise from the lower matrix stiffness experienced by the cells on the PDMS-PCL substrate.

Any of the embodiments defined by the dependent claims may be modified to form new embodiments by combining the limitations of any of the claims depending from a common parent, where possible. All such variants are considered to be within the scope of the disclosed subject matter.

The invention claimed is:

1. A method of improving cell expansion comprising culturing cells on a mesh substrate comprising fibers with a diameter of about 10 nm to about 1000 nm and a pore size of about 0.5 μm to about 100 μm, wherein said fibers comprise a mixture of polydimethylsiloxane and polycaprolactone in a ratio, and wherein said cells are T-cells.

2. The method of claim 1, wherein said mesh substrate comprises fibers with a diameter selected from the group consisting of about 100 nm to about 1000 nm, about 100 nm to about 2000 nm, about 500 nm to about 5000 nm, and about 1000 nm to about 5000 nm.

3. The method of claim 1, wherein said mesh substrate comprises fibers with a pore size selected from the group consisting of about 1 μm to about 100 μm, about 1 μm to about 50 μm, about 1 μm to about 10 μm, and about 1 μm to about 5 μm.

4. The method of claim 1, wherein said cells are
  i. isolated from an individual,
  ii. expanded in vitro, and
  iii. transfused back to an individual in need thereof.

5. The method of claim 4, wherein the bulk rigidity of fibers is greater than a local rigidity as indicated by atomic force microscopy indentation method.

6. The method of claim 5, wherein the bulk rigidity of fibers is at least twice as high as a local rigidity as indicated by atomic force microscopy indentation method.

7. The method of claim 6, where in the bulk elastic modulus of the fibers is less than 10 MPa.

8. The method of claim 6, where in the bulk elastic modulus of the fibers is between 3 and 6 MPa.

9. The method of claim 1, wherein said polydimethylsiloxane and polycaprolactone ratio (w/w) is selected from the group consisting of about 5:1, about 3:1, about 2.5:1, about 2:1, about 1:1, about 1:2, about 1:2.5, and about 1:5.

10. The method of claim 9, wherein said polydimethylsiloxane and polycaprolactone ratio (w/w) is about 1:1.

11. The method of claim 9, wherein said polydimethylsiloxane and polycaprolactone ratio (w/w) is about 2.5:1.

12. The method of claim 9, wherein said polydimethylsiloxane and polycaprolactone ratio (w/w) is about 3:1.

13. An article of manufacture, comprising: a mesh substrate comprising fibers with a diameter of about 10 nm to about 1000 nm and a pore size of about 0.5 μm to about 100 μm, wherein said fibers comprise a mixture of polydimethylsiloxane and polycaprolactone.

14. The article of claim 13, wherein the surface of the fibers is coated with a protein.

15. The article of claim 14, wherein the article is contained in a sterile container.

16. A method of improving stem cell expansion comprising culturing cells on a mesh substrate comprising fibers with a diameter of about 10 nm to about 1000 nm and a pore size of about 0.5 μm to about 100 μm, wherein said fibers comprise a mixture of polydimethylsiloxane and polycaprolactone in a ratio.

17. The method of claim 16, wherein said stem cell expansion on said mesh substrate is improved relative to a mesh substrate comprising polycaprolactone fibers alone.

18. The method of claim 17, wherein said stem cell expansion on said mesh substrate is improved relative to a mesh substrate comprising polycaprolactone fibers alone by at least about 20%.

19. The method of claim 17, wherein said stem cell expansion on said mesh substrate is improved relative to a mesh substrate comprising polycaprolactone fibers alone by at least about 40%.

20. The method of claim 16, wherein said polydimethylsiloxane and polycaprolactone ratio (w/w) is selected from the group consisting of about 5:1, about 3:1, about 2.5:1, about 2:1, about 1:1, about 1:2, about 1:2.5, and about 1:5.

21. The method of claim 20, wherein said polydimethylsiloxane and polycaprolactone ratio (w/w) is about 1:1.

22. The method of claim 20, wherein said polydimethylsiloxane and polycaprolactone ratio (w/w) is about 2.5:1.

23. The method of claim 20, wherein said polydimethylsiloxane and polycaprolactone ratio (w/w) is about 3:1.

24. The article of claim 13, wherein the diameter is about 500 nm to about 1000 nm.

25. The article of claim 24, wherein the pore size is about 1 um to about 50 μm.

26. The article of claim 14, wherein the protein is an antibody.

* * * * *